(12) United States Patent
Matsuda

(10) Patent No.: US 10,241,056 B2
(45) Date of Patent: Mar. 26, 2019

(54) INSPECTION APPARATUS, INSPECTION METHOD, AND PROGRAM

(71) Applicant: Keyence Corporation, Osaka (JP)

(72) Inventor: Hajime Matsuda, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 16/170,283

(22) Filed: Oct. 25, 2018

(65) Prior Publication Data

US 2019/0064078 A1    Feb. 28, 2019

Related U.S. Application Data

(63) Continuation of application No. 16/009,244, filed on Jun. 15, 2018, which is a continuation of application (Continued)

(30) Foreign Application Priority Data

Jun. 9, 2014    (JP) .................................. 2014-119102

(51) Int. Cl.
     *G01N 21/80*      (2006.01)
     *G01N 21/88*      (2006.01)
     (Continued)

(52) U.S. Cl.
     CPC ..... *G01N 21/8806* (2013.01); *G01N 21/8851* (2013.01); *G06K 9/2027* (2013.01);
     (Continued)

(58) Field of Classification Search
     CPC ........... G01N 21/8806; G01N 21/8851; G01N 2201/12; G01N 2021/845; G01N 21/55; G01N 2201/062; G01N 21/57; G01N 2201/06; G01N 2021/4735; G01N 21/88; G01N 21/8803; G01N 21/89; G01N 2201/061; G01N 2021/4711;
     (Continued)

(56) References Cited

U.S. PATENT DOCUMENTS

| | | | |
|---|---|---|---|
| 5,016,173 | A | 5/1991 | Kenet et al. |
| 8,943,779 | B2 | 2/2015 | Amano et al. |

(Continued)

FOREIGN PATENT DOCUMENTS

| | | | |
|---|---|---|---|
| JP | H05-164550 A | 6/1993 | |
| JP | 2001-074430 A | 3/2001 | |

(Continued)

*Primary Examiner* — Michael P Stafira
(74) *Attorney, Agent, or Firm* — Kilyk & Bowersox, P.L.L.C.

(57) ABSTRACT

To facilitate adjusting of a distance from an inspection target to an illumination section by providing a movable illumination section that is movable independently of the imaging section. An illumination apparatus has a plurality of LEDs arranged in a substantially annular form, a light diffusion member for diffusing light emitted from the plurality of LEDs, and a lighting control part for lighting the plurality of light sources in accordance with a predetermined lighting pattern when designated to start lighting. In particular, the illumination apparatus moves independently of a camera to adjust a distance to a workpiece.

6 Claims, 32 Drawing Sheets

Related U.S. Application Data

No. 15/686,185, filed on Aug. 25, 2017, now Pat. No. 10,036,713, which is a continuation of application No. 15/586,303, filed on May 4, 2017, now Pat. No. 9,778,203, which is a continuation of application No. 15/290,020, filed on Oct. 11, 2016, now Pat. No. 9,689,806, which is a continuation of application No. 14/718,113, filed on May 21, 2015, now Pat. No. 9,494,528.

(51) Int. Cl.
    *G06K 9/32*     (2006.01)
    *G06K 9/20*     (2006.01)
    *G06T 7/00*     (2017.01)
    *G06T 7/586*     (2017.01)
    *G01N 21/84*     (2006.01)

(52) U.S. Cl.
CPC ............ *G06K 9/325* (2013.01); *G06T 7/0004* (2013.01); *G06T 7/0008* (2013.01); *G06T 7/586* (2017.01); *G01N 2021/845* (2013.01); *G01N 2201/062* (2013.01); *G01N 2201/12* (2013.01); *G06T 2207/10152* (2013.01); *G06T 2207/20016* (2013.01); *G06T 2207/20221* (2013.01); *G06T 2207/30164* (2013.01)

(58) Field of Classification Search
CPC ... G01N 2021/4723; G01N 2021/4783; G01N 2021/8883; G01N 2021/8917; G01N 21/255; G01N 21/27; G01N 21/3586; G01N 21/4738; G01N 21/474; G01N 21/8901; G01N 21/892; G01N 21/94; G01N 21/9501; G01N 2201/0221; G01N 22/00; G01B 11/2513; G01B 11/2509; G01B 11/005; G01B 11/303; G01B 21/047; G01B 2210/58; G01B 5/008; G01B 5/012; G01B 11/24; G01B 11/25; G01B 11/0608; G01B 11/0691; G01B 11/22; G01B 11/245; G02B 2027/0138; G02B 27/0172; G02B 2027/014; G02B 2027/0178; G02B 2027/0187; G02B 21/06; G02B 21/084; G02B 21/125; G02B 21/26; G02B 21/361; G02B 21/367; G02B 27/0075; G02B 27/017; G02B 27/4205; G02B 5/005; G02B 6/0003; G02B 6/0008; G02B 7/285; G02B 7/32; G02B 7/36; G02B 7/40

See application file for complete search history.

(56) References Cited

U.S. PATENT DOCUMENTS

| | | | |
|---|---|---|---|
| 9,494,528 | B2 | 11/2016 | Matsuda |
| 9,689,806 | B2 | 6/2017 | Matsuda |
| 9,778,203 | B2 | 10/2017 | Matsuda |
| 10,036,713 | B2 | 7/2018 | Matsuda |
| 2003/0184740 | A1 | 10/2003 | Paradis |
| 2010/0246174 | A1* | 9/2010 | Ido ............... G01N 21/8806 362/235 |
| 2014/0152990 | A1* | 6/2014 | Ehbets ............. G01J 3/50 356/405 |
| 2015/0355104 | A1 | 12/2015 | Matsuda |
| 2017/0030839 | A1 | 2/2017 | Matsuda |
| 2017/0350827 | A1 | 12/2017 | Matsuda |
| 2018/0292327 | A1 | 10/2018 | Matsuda |

FOREIGN PATENT DOCUMENTS

| | | |
|---|---|---|
| JP | 2007-206797 | 8/2007 |
| JP | 2007-327848 A | 12/2007 |
| JP | 2009-512049 A | 3/2009 |
| JP | 2010-237034 A | 10/2010 |
| JP | 2011-009232 A | 1/2011 |
| JP | 2012-083282 A | 4/2012 |
| JP | 2013-096784 A | 5/2013 |
| JP | 2013-140040 A | 7/2013 |
| JP | 2013-167448 A | 8/2013 |
| JP | 2013-205041 A | 10/2013 |

\* cited by examiner $$\begin{pmatrix} I_1 \\ I_2 \\ I_3 \\ I_4 \end{pmatrix} = \rho L \begin{pmatrix} s_{11} & s_{12} & s_{13} \\ s_{21} & s_{22} & s_{23} \\ s_{31} & s_{32} & s_{33} \\ s_{41} & s_{42} & s_{43} \end{pmatrix} \begin{pmatrix} n_x \\ n_y \\ n_z \end{pmatrix} \quad \cdots \text{EXPRESSION 1}$$

$$z_{x,y}^{n+1} = \frac{1}{4}\left(z_{x+1,y}^n + z_{x,y+1}^n + z_{x-1,y}^n + z_{x,y-1}^n\right) \\ - \frac{w}{8}\left(p_{x+1,y} - p_{x-1,y} + q_{x,y+1} - q_{x,y-1}\right)$$

$\cdots$ EXPRESSION 2

INSPECTION APPARATUS, INSPECTION METHOD, AND PROGRAM

CROSS-REFERENCE TO RELATED APPLICATIONS

The present application is a continuation of U.S. patent application Ser. No. 16/009,244 filed Jun. 15, 2018 which is a continuation of U.S. patent application Ser. No. 15/686,185 filed Aug. 25, 2017, now U.S. Pat. No. 10,036,713, which in turn is a continuation of U.S. patent application Ser. No. 15/586,303 filed May 4, 2017, now U.S. Pat. No. 9,778,203, which in turn is a continuation of U.S. patent application Ser. No. 15/290,020, filed Oct. 11, 2016, now U.S. Pat. No. 9,689,806, which in turn is a continuation of U.S. patent application Ser. No. 14/718,113, filed May 21, 2015, now U.S. Pat. No. 9,494,528, which claims foreign priority based on Japanese Patent Application No. 2014-119102, filed Jun. 9, 2014, the contents of which are incorporated herein by reference.

BACKGROUND OF THE INVENTION

1. Field of the Invention

The present invention relates to an inspection apparatus, an inspection method, and a program.

2. Description of Related Art

In order to measure an accurate three-dimensional shape of a workpiece (inspection target product) by using a photometric stereo principle, there is required an illumination light source whose illumination light is incident on each surface of the workpiece with a uniform light amount. Further, an angle of incidence of the illumination light is required to be known. Moreover, since the angle of incidence of light should not change in accordance with a region of the workpiece, there is required an illumination light source having a size corresponding to the size of the workpiece to be inspected. Furthermore, scale information (actual dimension per pixel) of an image captured by a camera is also required. A visual inspection apparatus is often installed by a user, and it is difficult for the user to satisfy these strict installation conditions. Therefore, according to JP 2007-206797 A, a dedicated apparatus formed by integrating illumination and a camera is proposed, to thereby reduce a burden of installation of the user.

In JP 2007-206797 A, the workpiece 2 is irradiated with parallel light by each of four spot illumination light sources, but a shadow is apt to occur due to the spot illumination. Hence, many regions in the surface of the workpiece are not measurable depending on the type or the placement of workpiece. Such a problem is reduced if an illumination apparatus can be brought away from the workpiece to use regular reflective light, or brought close to the workpiece to use diffused reflective light, in accordance with the type or the placement of the workpiece.

However, in JP 2007-206797 A, since the illumination apparatus and the camera are integrated, arrangement of the illumination apparatus cannot be adjusted in accordance with the type or the placement of the workpiece.

SUMMARY OF THE INVENTION

Therefore, an object of the present invention is to facilitate adjusting of a distance from an inspection target to an illumination section by providing an illumination section that is movable independently of the imaging section.

According to the present invention, for example, there is provided an inspection apparatus including: an imaging section for capturing an image of an inspection target; an illumination section which has a plurality of light sources arranged in a substantially annular form, a light diffusion member for diffusing light emitted from the plurality of light sources, and a lighting control part for lighting the plurality of light sources in accordance with a predetermined lighting pattern when designated to start lighting, and which moves independently of the imaging section to adjust a distance to the inspection target; an inspection image generating section for synthesizing a plurality of luminance images, acquired by the imaging section, by a photometric stereo method, to generate an inspection image having a plurality of pixel values in accordance with inclination or a reflectance of a surface of the inspection target; and a determination section for determining defectiveness/non-defectiveness of the inspection target by using the inspection image.

According to the present invention a distance from an inspection target to an illumination section can be adjusted by providing an illumination section that is movable independently of the imaging section. Hence, it is possible to bring the illumination section away from a workpiece to use regular reflective light, or bring the illumination section close to the workpiece to use diffused reflective light, in accordance with the type or the placement of the workpiece.

BRIEF DESCRIPTION OF THE DRAWINGS

FIG. 22 is a view showing one example of the user interface;

DETAILED DESCRIPTION OF PREFERRED EMBODIMENT

Hereinafter, one embodiment of the present invention is shown. An individual embodiment described below will be useful for understanding a variety of concepts such as a superordinate concept, an intermediate concept, and a subordinate concept of the present invention. Further, a technical range of the present invention is defined by the claims, and is not limited by the following individual embodiment.

Figure 1:
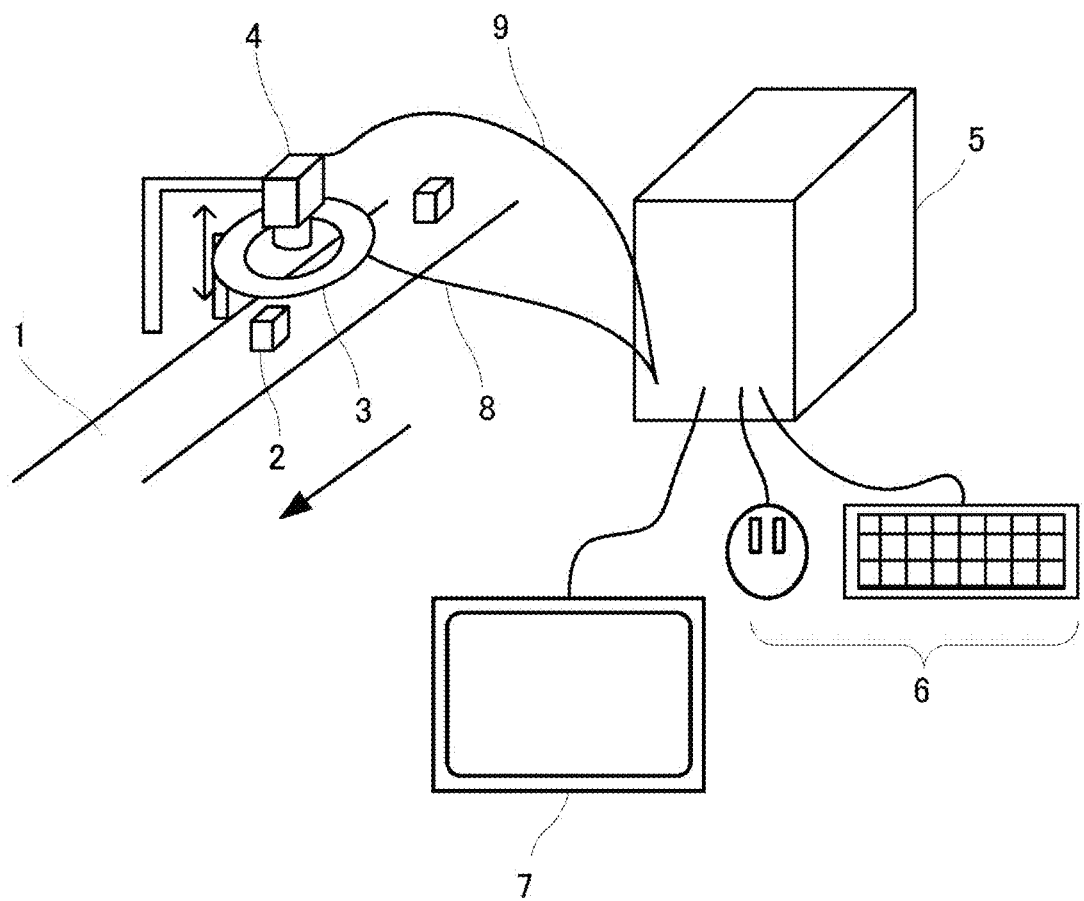
FIG. 1 is a view showing an outline of an inspection apparatus.

FIG. 1 is a view showing one example of a visual inspection system. A line 1 is a conveyer belt for conveying a workpiece 2 which is an inspection target. An illumination apparatus 3 is one example of an illumination section for illuminating an inspection target in accordance with a photometric stereo method. A camera 4 is one example of an imaging section for receiving reflective light from the illuminated inspection target to generate a luminance image in accordance with the photometric stereo method. An image processing apparatus 5 is a visual inspection apparatus for calculating a normal vector of the surface of the workpiece 2 from a plurality of luminance images acquired by the camera 4, performing accumulation computing of a pixel value of a pixel of interest by using a normal vector of a pixel adjacent to the pixel of interest with respect to an inclination image made up of pixel values based on the normal vector calculated from the plurality of luminance images and a reduced image of the inclination image, and generating an inspection image having the pixel value, to determine defectiveness/non-defectiveness of the inspection target by using the inspection image. The inclination image may be referred to as a normal vector image. The image processing apparatus 5 may create a reflectance image (albedo image) from the luminance image. A display part 7 displays a user interface for setting a control parameter related to inspection, an inclination image, a reflectance image, an inspection image and the like. An input part 6 is a console, a pointing device, and a keyboard, and is used for setting a control parameter. The image processing apparatus 5 and the illumination apparatus 3 are connected by a signal line 8. The image processing apparatus 5 and the camera 4 are connected by a signal line 9.

In particular, according to FIG. 1, the camera 4 and the illumination apparatus 3 are supported by respectively different frames so as to be independently movable. Since the illumination apparatus 3 is movable independently of the camera 4, it is possible to freely adjust a distance from the workpiece 2 to the illumination apparatus 3. That is, since the illumination apparatus 3 is brought away from the workpiece 2 in accordance with the type or the placement of the workpiece 2, the camera 4 can intensely receive regular reflective light. Further, since the illumination apparatus 3 is brought close to the workpiece 2, the camera 4 can intensely receive diffused reflective light. The camera 4 and the illumination apparatus 3 may be supported by the same frame. In this case, the illumination apparatus 3 may be fixed to the frame by means of a clamping mechanism for adjusting an installation position of the illumination apparatus 3.

<Photometric Stereo Principle>

Figures 2A, 2B, 2C:
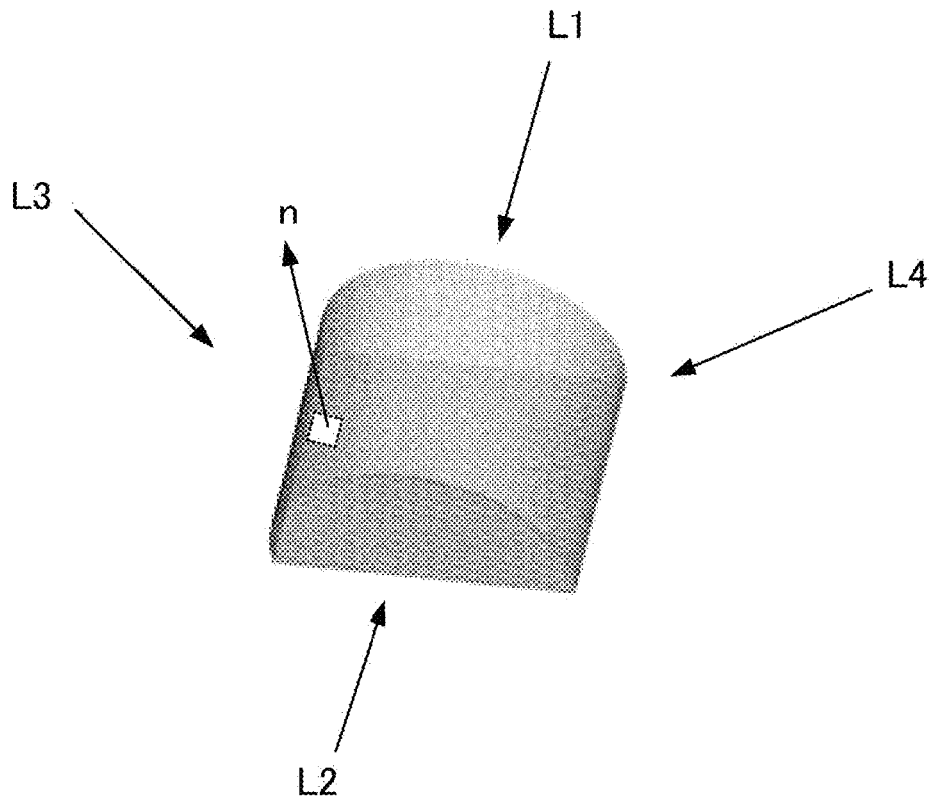
FIGS. 2A to 2C provide a view for describing a photometric stereo principle.

In a general photometric stereo method, as shown in FIG. 2A, illumination light L1 to illumination light L4 are applied to the workpiece 2 from four directions while being switched, to generate four luminance images. The direction of the illumination light used at the time of capturing each luminance image is in only one direction. Note that a luminance image is made up of a plurality of pixels, and four pixels whose coordinates match in the four luminance images correspond to the same surface of the workpiece. Expression 1 shown in FIG. 2B is established among pixel values (luminance values) I1, I2, I3, I4 of the four pixels and the normal vector n. Here, $\rho$ is a reflectance. L is a light amount of the illumination light from each direction, and is known. Here, the light amounts from the four directions are the same. S is an illumination-direction matrix, and is known. By solving this mathematical expression, the reflectance $\rho$ and the normal vector n for each coordinates (surface of the workpiece) are obtained. As a result, a reflectance image and an inclination image are obtained.

In the present embodiment, further, a height component is extracted from the inclination image to create, as the inspection image, a shape image showing a shape of the workpiece. The inspection image is obtained by an accumulation computing equation which is Expression 2 shown in FIG. 2C. Here, zn is a result of n-th accumulation and shows the shape of the surface of the workpiece, x and y indicate coordinates of a pixel, and n shows how many times iteration calculation has been performed. Moreover, p shows an inclination component in a horizontal direction, q shows an inclination component in a vertical direction, p and q are obtained from the normal vector n, and w is weight. Further, a 1/1-inclination image is used in first accumulation computing, a ½-reduced inclination image is used in second accumulation computing, and a ¼-reduced inclination image is used in third accumulation computing. At the time of creating the reduced image, reduction processing may be performed after Gaussian processing is performed.

In the present embodiment, a parameter called a characteristic size is adopted in the accumulation computing. The characteristic size is a parameter for giving weight to a component of a reduced image to be used in the accumulation computing. The characteristic size is a parameter showing a size of a surface shape of the workpiece 2. For example, when the characteristic size is 1, weight with respect to four pixels adjacent to a pixel of interest in an x-y direction is set the largest and the accumulation computing is performed. When the characteristic size is 2, weight with respect to eight pixels adjacent to the pixel of interest in the x-y direction is set the largest and the accumulation computing is performed. However, since computing using the eight pixels causes an increase in computing amount, the foregoing reduced image is created and used for the computing. That is, in place of using the eight adjacent pixels, the inclination image is reduced into ½ and the computing is performed. Thereby, concerning a certain pixel of interest, four pixels in the reduced image may be considered for the computing. Also when the characteristic size is increased to 4, 8, 16, and 32, reduced images corresponding thereto are created, and weight with respect to the reduced image corresponding to the characteristic size is set the largest, whereby a similar effect of reduction in computing load can be obtained.

Figure 3:
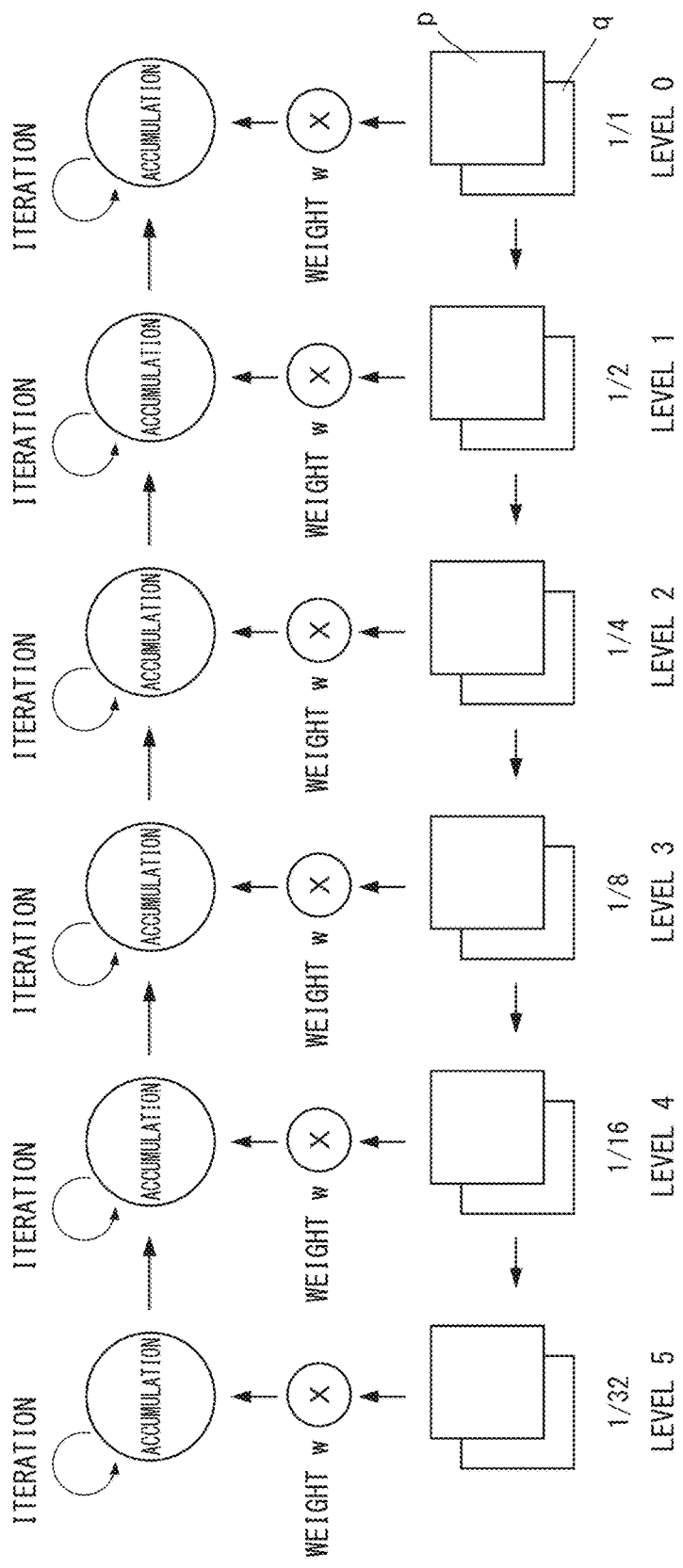
FIG. 3 is a diagram for describing accumulation computing.

FIG. 3 shows one example of the accumulation computing. In this example, two inclination images (an image with a horizontal inclination component p and an image with a vertical inclination component q) obtained from the normal vector n are inputted. First, a whole shape is accumulated by an inclination image with a large reduction degree, and a fine shape is accumulated by an image with a smaller reduction degree. This allows restoration of the whole shape in a short period of time. According to FIG. 3, for example, with respect to the 1/32-reduced image, z which is a parameter indicating the shape of the surface of the workpiece concerning the pixel of interest is calculated by Expression 2. The weight w is decided in accordance with the characteristic size. Each pixel constituting the reduced image is taken as a pixel of interest, and the accumulation computing is subjected to iteration (repetition processing). An initial value of z is zero. Then, z is calculated with respect to the 1/16-reduced image in accordance with Expression 2. Here, an inclination component of the 1/16-reduced image is accumulated on a result of the computing of 1/32. Similarly, the accumulation computing is performed from the 1/8-reduced image to the 1/1-image.

Figure 4:
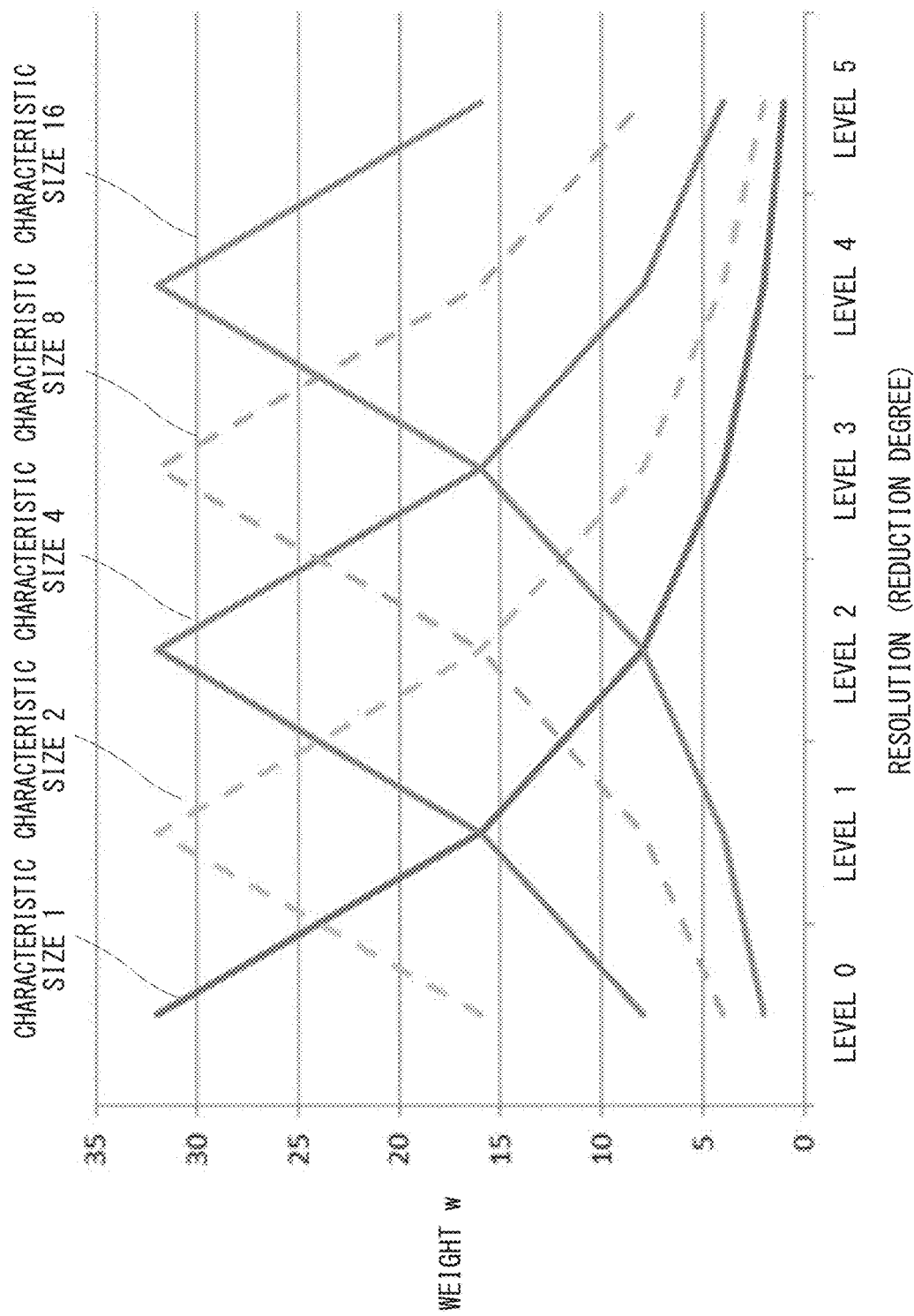
FIG. 4 is a diagram showing a method for deciding weight based on a characteristic size.

FIG. 4 shows one example of weight with respect to each characteristic size. A horizontal axis indicates a resolution level (reduction degree), and a vertical axis indicates weight. As can be seen from FIG. 4, in the characteristic size 1, weight is the largest at level 0 (1/1-image) with the smallest reduction degree. This allows accumulation of a finer shape. In the characteristic size 2, weight is the largest at level 1 (½-image). This allows further accumulation of a shape having a larger size. As thus described, each weight is decided such that a peak is generated at the level corresponding to the characteristic size.

As a method for restoring the shape image, other than the above accumulation computing, it is also possible to adopt known Fourier transform integration ("A Method for Enforcing Integrability in Shape from Shading Algorithms", IEEE Transactions on Pattern Analysis and Machine Intelligence, Vol. 10, No. 4 Jul. 1988). Also in this method, it is possible to change a characteristic size to be extracted by generating a reduced image in a calculation process and adjusting a weighting component.

Figure 5:
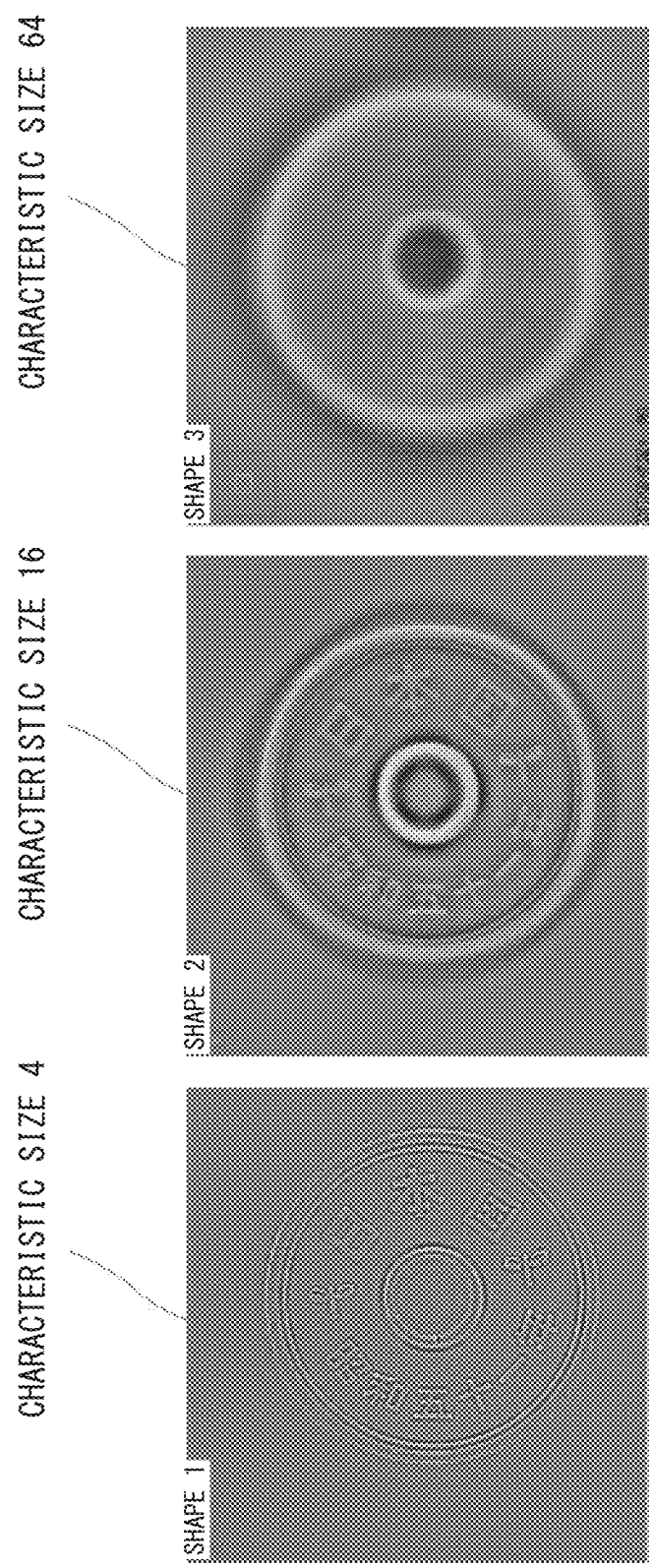
FIG. 5 is a view showing one example of inspection images with different characteristic sizes.

FIG. 5 shows one example of inspection images in accordance with differences in characteristic size. It can be seen that a fine shape is extracted in the characteristic size 4, a whole shape is extracted in the characteristic size 64, and a shape of an intermediate size therebetween is extracted in the characteristic size 16. In such a manner, a small characteristic size is useful for inspecting a fine flaw, a large characteristic size is suitable for discriminating the presence or absence of an object, and an intermediate characteristic size is suitable for OCR of an uneven character, and the like. That is, selecting a suitable characteristic size in accordance with the inspection tool can improve the inspection accuracy.

Figure 6:
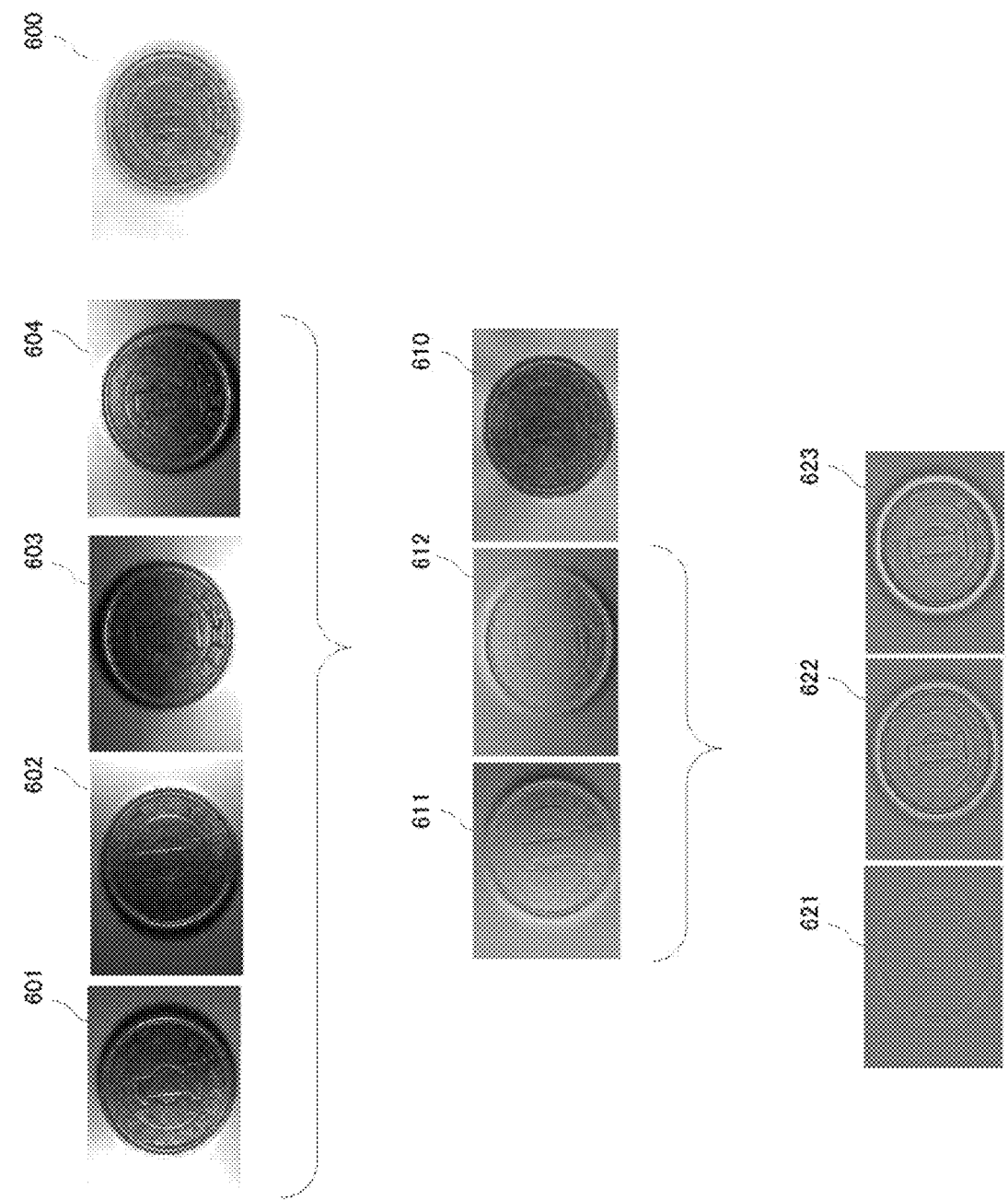
FIG. 6 is a view describing images related to generation of a surface shape image.

FIG. 6 is a view showing a step of creating an inspection image by the photometric stereo method. Luminance images 601 to 604 are luminance images acquired by illuminating the workpiece 2 with illumination light from respectively different illumination directions. Note that a luminance image 600 is a luminance image obtained by simultaneously illuminating the workpiece 2 from four directions. A normal vector of the surface of the workpiece is obtained by computing from the plurality of luminance images acquired by illuminating the workpiece 2 with the illumination light from the respectively different illumination directions. An inclination image 611 is an inclination image whose pixel value is an inclination component in an x-direction of the normal vector obtained from the luminance images 601 to 604. An inclination image 612 is an inclination image whose pixel value is an inclination component in a y-direction of the normal vector obtained from the luminance images 601 to 604. A reflectance image 610 is a reflectance image obtained by removing an amount of change in luminance value due to inclination of the surface of the workpiece from the normal vector obtained from the luminance images 601 to 604, to form an image with a reflectance of the surface of the workpiece. Inspection images 621 to 623 are images (surface shape images) with respectively different characteristic sizes obtained from the inclination images 611, 612. Each of the inspection images 621 to 623 is also made up of pixels based on an inclination component, and is thus a type of the inclination image. In such a procedure, the inspection image of the workpiece 2 is generated. Note that the luminance image 600 or the reflectance image 610 as an all-directional illumination image may be adopted as the inspection image, depending on the inspection tool. The all-directional illumination image is a luminance image acquired by lighting all of a plurality of light sources provided in the illumination apparatus 3.

<Texture Information>

Figure 7:
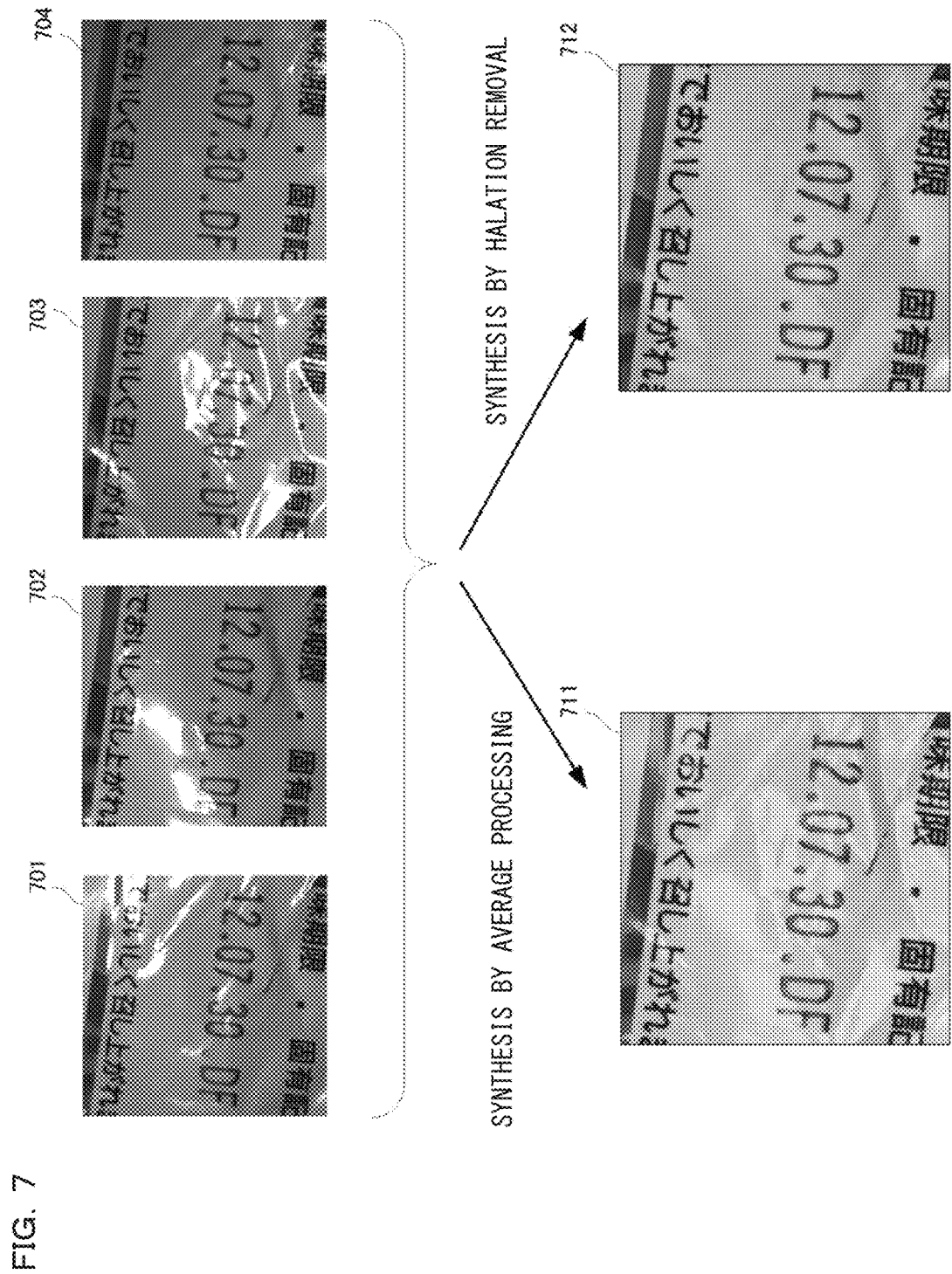
FIG. 7 is a view describing a method for generating a texture image.

Texture information is information based on the reflectance ρ of the surface of the workpiece 2. The reflectance ρ is obtained by Expression 1, namely, one reflectance image is obtained from four luminance images. The reflectance image is an image having a pixel value proportional to the reflectance ρ of the surface of the workpiece. As shown in FIG. 7, a normal vector is calculated from four luminance images 701 to 704, and based on the calculated normal vector and a luminance value of a pixel corresponding to each of the plurality of luminance images, a pixel value proportional to a reflectance of each pixel is calculated, to obtain texture images 711, 712 which are reflectance images. Examples of this generation method includes a method of averaging pixels of the four luminance images to obtain a texture image, and a method of removing halation from the four luminance images and then averaging pixels to obtain a texture image. The texture image 711 is one example of the image obtained by averaging pixels, and the texture image 712 is one example of the image obtained by removing halation. In the four luminance images, four pixels whose coordinates match exist. It is possible to remove halation by removing a pixel with the largest pixel value out of the four pixels, or by removing pixels with the largest to N-th largest pixel values (N is a natural number not larger than 3). This is because halation appears as high luminance in the image.

Since both the texture images 711, 712 are made up of pixels based on the reflectance, each of them is one type of the reflectance image.

<Function Block>

Figure 8:
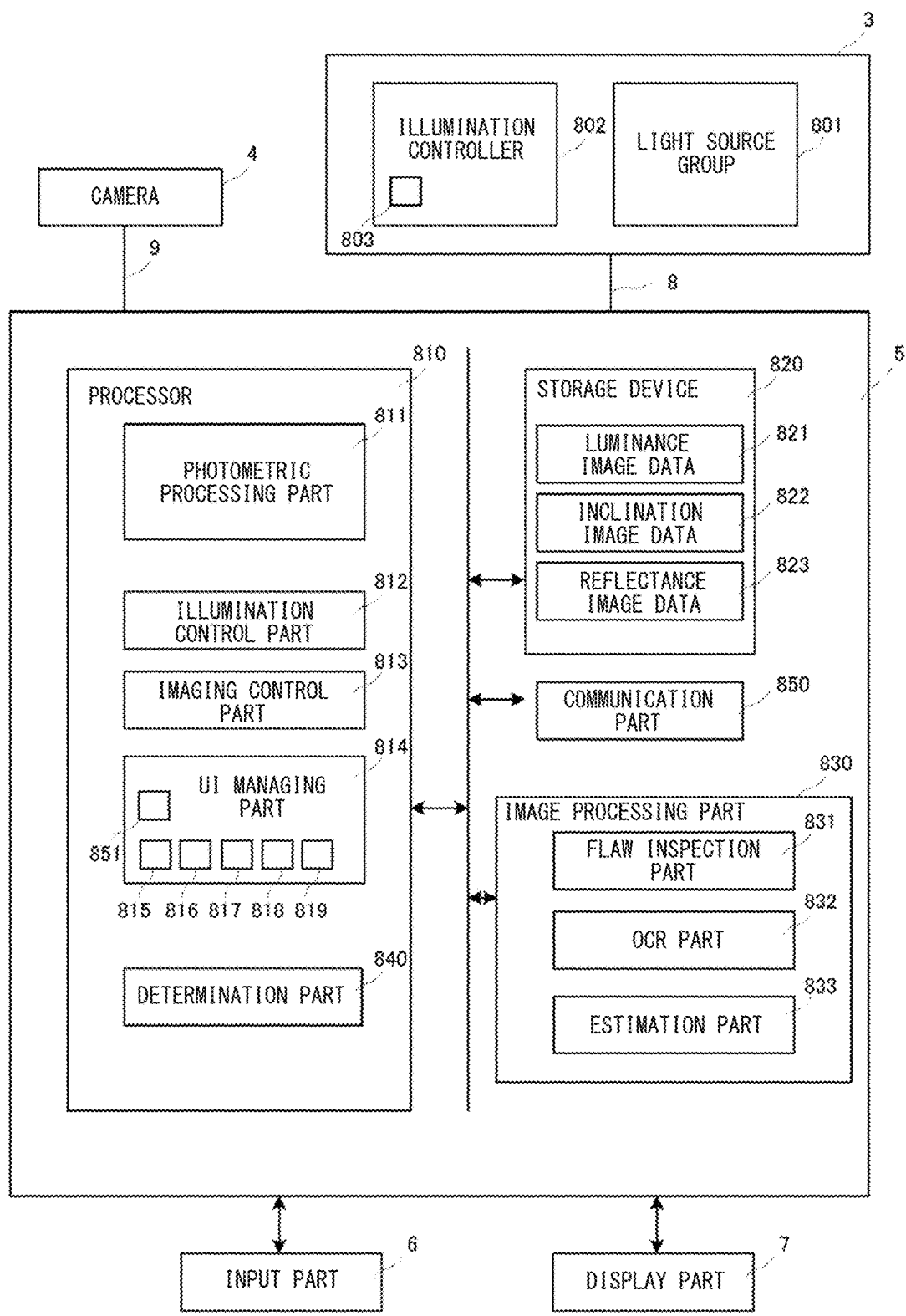
FIG. 8 is a function block diagram of the inspection apparatus.

FIG. 8 is a block diagram of the inspection apparatus. In this example, the illumination apparatus 3, the camera 4, and the image processing apparatus 5 are respectively housed in separate housings, but this is merely an example, and the illumination apparatus 3, the camera 4, and the image processing apparatus 5 may be integrated as appropriate. The illumination apparatus 3 is one example of the illumination section for illuminating the inspection target in accordance with the photometric stereo method, and provided with a light source group 801 and an illumination controller 802 for controlling this light source group. One segment may be formed of a plurality of light-emitting elements, and the light source group 801 may be formed of a plurality of segments. The number of segments is generally four, but may be any number as long as it is not smaller than three. This is because an inspection image can be generated by the photometric stereo method if the workpiece 2 can be illuminated from three or more illumination directions. As shown in FIG. 1, an outer shape of the illumination apparatus 3 may be a ring shape. Further, the illumination apparatus 3 may be configured by a plurality of illumination units each separated from one another. For example, although illumination units that are used for capturing an image of the workpiece 2 exist in the market, these illumination units are not developed for photometric stereo. However, the illumination apparatus 3 may be configured by preparing a plurality of such illumination units and connecting an illumination controller for controlling these illumination units. The illumination controller 802 controls lighting timing and an illumination pattern (lighting pattern) of the light source group 801 in accordance with a control command from the image processing apparatus 5. Although a description will be given assuming that the illumination controller 802 is incorporated in the illumination apparatus 3, the illumination controller 802 may be incorporated in the camera 4 or in the image processing apparatus 5, or may be housed in a housing independent of these.

The camera 4 is one example of the imaging section for receiving reflective light from the illuminated inspection target to generate a luminance image in accordance with the photometric stereo method, and performs the imaging processing in accordance with a control command from the image processing apparatus 5. The camera 4 may create a luminance image of the workpiece 2 and transmit the luminance image to the image processing apparatus 5, or the camera 4 may transmit a luminance signal obtained from an imaging element to the image processing apparatus 5 and the image processing apparatus 5 may generate a luminance image. Since the luminance signal is a signal used for generating the luminance image, the luminance signal is also the luminance image in a broad sense.

The image processing apparatus 5 is one type of computer, and has a processor 810 such as a CPU and an ASIC, a storage device 820 such as a RAM, a ROM, and a portable storage medium, an image processing part 830 such as an ASIC, and a communication part 850 such as a network interface. The processor 810 serves to set an inspection tool, adjust a control parameter, and generate/regenerate/update an inspection image. A photometric processing part 811 functions as a computing section (inspection image generating section) for calculating the normal vector n of the surface of the workpiece 2 from a plurality of luminance images acquired by the camera 4, and performing accumulation computing of a pixel value of a pixel of interest by using the normal vector n of a pixel adjacent to the pixel of interest with respect to an inclination image having a pixel value based on the normal vector n calculated from the plurality of luminance images and a reduced image of the inclination image, to generate an inspection image having the pixel value. Note that, specifically, the inspection image is generated by using the foregoing mathematical expression or the like. An illumination control part 812 transmits a control command to the illumination controller 802 to control a lighting pattern, illumination switching timing, or the like. An imaging control part 813 controls the camera 4. A UI managing part 814 displays on the display part 7 a user interface (UI) for setting an inspection tool, a UI for setting a parameter required for generating an inspection image, and the like, and sets the inspection tool and the parameter in accordance with information inputted from the input part 6. In particular, a characteristic size setting part 815 functions as a setting section for setting a characteristic size which is a parameter for giving weight w to a component of a reduced image that is used in the accumulation computing. An image selection part 816 selects an image to be displayed or the like, out of a plurality of luminance images, a plurality of inspection images, a plurality of inclination images, and a plurality of reflectance images. The image selection part 816 may select an image, which is to be saved or outputted, out of the plurality of luminance images acquired by the camera 4 and the inspection image. An inspection tool setting part 817 sets an inspection tool for the inspection image selected by the image selection part 816. The inspection tool setting part 817 sets a flaw inspection region, or sets a character recognition region, for the reference image. A reference image setting part 818 sets a reference image as an inspection image acquired from a non-defective product. A display control part 851 switches and displays the luminance image and the inspection image on the display part 7, or simultaneously displays the luminance image and the inspection image. Further, when the control parameter is adjusted, the display control part 851 updates the image being displayed on the display part 7 to a display where the control parameter has been reflected. An inspection tool setting part 817 may include the display control part 851, the characteristic size setting part 815, the image selection part 816, the reference image setting part 818, and a condition setting part 819. The image processing part 830 functions as an inspection region setting section for executing a pattern search on an inspection image by using the reference image, to set an inspection region (e.g., flaw inspection region, character recognition region, and the like) in the inspection image. The inspection region is, for example, a character recognition region. The condition setting part 819 sets a condition for outputting an image to an external device connected to the display part 7 or the communication part 850, or sets a condition for saving an image into a portable storage medium. A determination part 840 functions as a determination section for determining defectiveness/non-defectiveness of the workpiece 2 by using the inspection image. For example, the determination part 840 receives a result of the inspection executed in the image processing part 830 by using the inspection image and determines whether or not the inspection result satisfies a non-defective product condition (tolerance or the like).

The storage device 820 stores luminance image data 821 which is data of the luminance image acquired by the camera 4, and inclination image data 822 and reflectance image data 823 generated by the photometric processing part 811. Further, the storage device 820 also stores a variety of setting data, a program code for generating a user interface, and the like. The storage device 820 may store and hold inspection images with respectively different characteristic sizes. Further, in addition to the inspection image, the storage device 820 may also store inclination image data or reflectance image data used for generating the inspection image. When erroneous determination on the workpiece 2 is found, these pieces of data may be useful for specifying which of the inspection image, the inclination image and the reflectance image has a problem and correcting its control parameter.

The image processing part 830 executes visual inspection by using the inspection image (the inclination image data 822, the reflectance image data 823) generated by the photometric processing part 811. A flaw inspection part 831 executes flaw inspection in flaw inspection regions of a plurality of inspection images generated by using respectively different characteristic sizes. An OCR part 832 functions as a character recognition processing section for performing character recognition processing on a plurality of inspection images generated by using respectively different characteristic sizes. The flaw inspection part 831 and the OCR part 832 may read the inspection image (the inclination image data 822, the reflectance image data 823) stored in the storage device 820 and execute inspection in the character recognition region, to write an inspection result into the storage device 820 or to pass the inspection result to the determination part 840. The determination part 840 determines defectiveness/non-defectiveness of the workpiece 2 based on this inspection result.

<Setting Mode>

The inspection system has a setting mode for setting an inspection tool and an inspection mode (operation mode) for executing a visual inspection of the workpiece 2 in accordance with the set inspection tool. Here, one example of the setting mode will be described.

Figure 9:
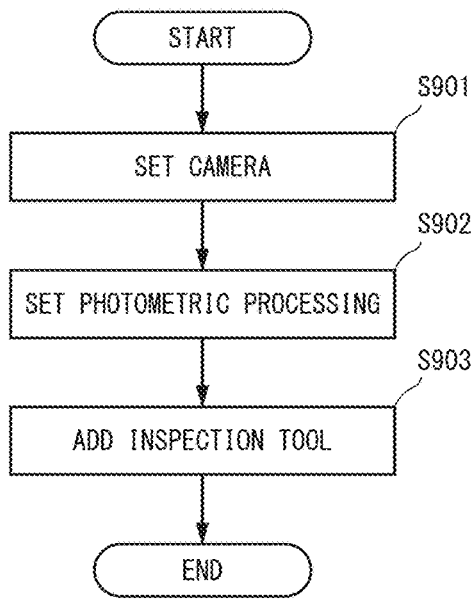
FIG. 9 is a flowchart showing a setting mode.

FIG. 9 is a flowchart concerning the setting mode. When the start of the setting mode is designated through the input part 6, the UI managing part 814 of the processor 810 displays a UI for setting the inspection tool on the display part 7.

Figure 10:
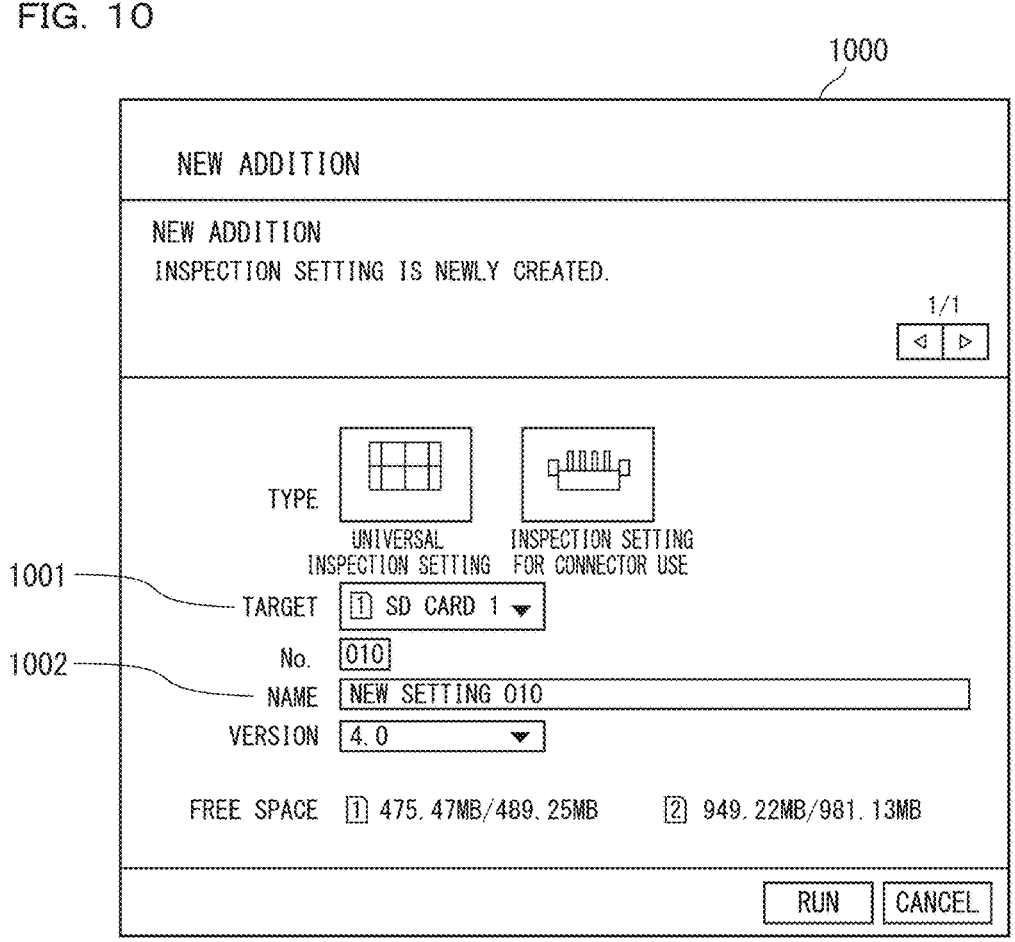
FIG. 10 is a view showing one example of a user interface.

FIG. 10 shows one example of the UI. A UI 1000 displayed on the display part 7 by the UI managing part 814 is provided with a pull-down menu 1001 for designating a saving destination of an inspection result, and a text box 1002 for inputting a name of the inspection tool. When detecting pressing-down of a run button, the UI managing part 814 displays the next UI.

Figure 11:
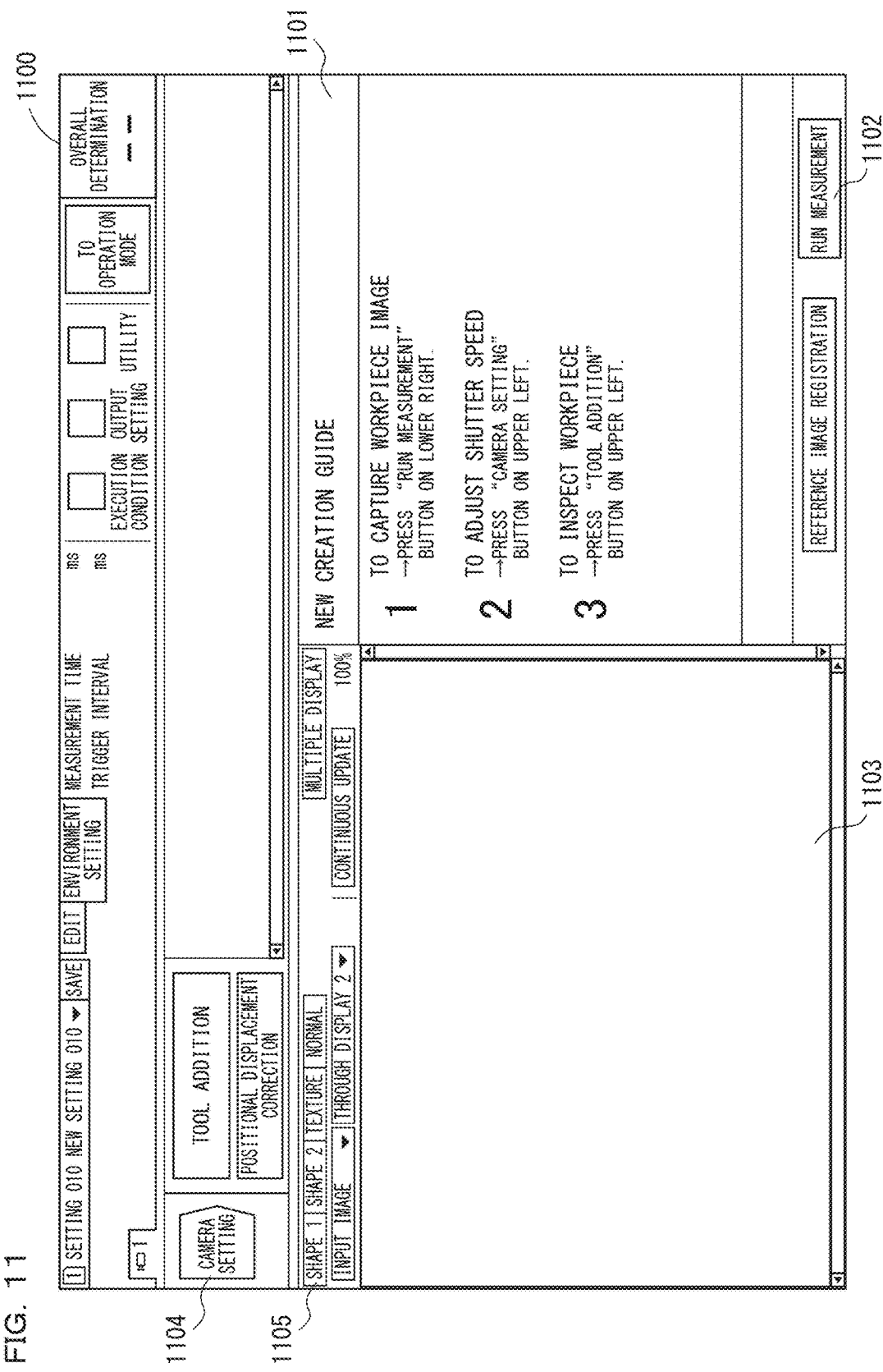
FIG. 11 is a view showing one example of the user interface.

A UI 1100 shown in FIG. 11 has guidance 1101 for setting the inspection tool, a measurement run button 1102 for designating the camera 4 to perform imaging, a display region 1103 for displaying an image captured by the camera 4, and a camera setting button 1104 for designating the start of setting of the camera. An image selection part 1105 is a button for selecting an image to be displayed in the display region 1103 or an image to be used for the inspection. In this example, any one image out of a shape 1, a shape 2, a texture, and normal is optionally selected by the image selection part 1105. When the measurement run button 1102 is operated, the imaging control part designates the camera 4 to perform imaging. The UI managing part 814 renders a luminance image acquired by the camera 4 to the display region 1103. Note that, when another image is selected by the image selection part 1105, the UI managing part 814 renders the image selected by the image selection part 1105 to the display region 1103. As thus described, the user can switch an image displayed in the display region 1103 by operating the image selection part 1105 or designating switching of the image through the input part 6. When the camera setting button 1104 is operated, the UI managing part 814 performs switching to the next UI.

Figure 12:
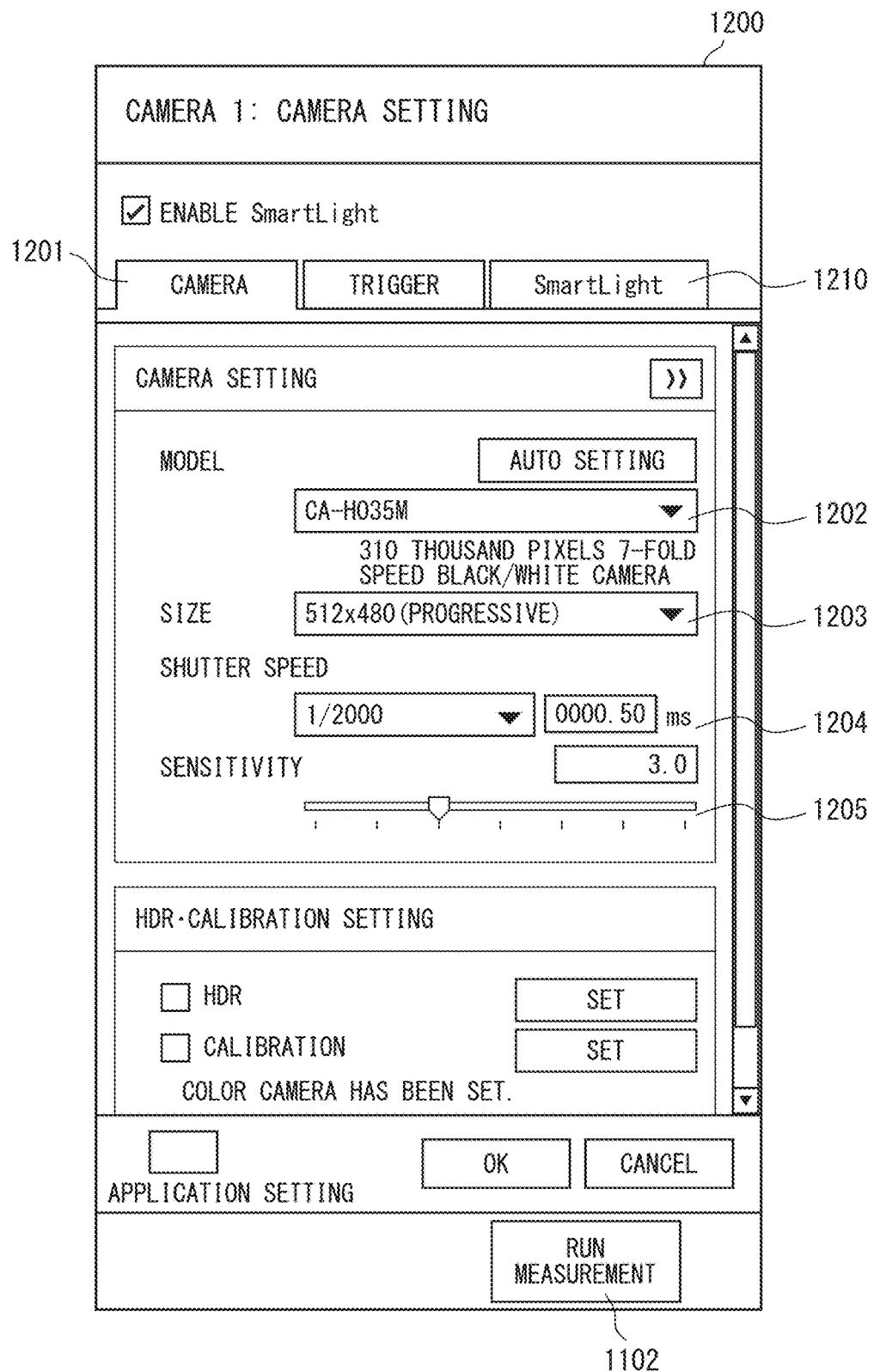
FIG. 12 is a view showing one example of the user interface.

In S901, the UI managing part 814 displays a UI for setting the camera 4 on the display part 7, to execute setting of the camera. FIG. 12 shows one example of a camera setting UI 1200. A camera setting tab 1201 has a pull-down menu 1202 for setting a model of a camera, a pull-down menu 1203 for setting an image size, a pull-down menu 1204 for setting a shutter speed, and a slider 1205 for setting the sensitivity of the camera. When the measurement run button 1102 is operated, the UI managing part 814 displays in the display region 1103 a luminance image acquired by the camera 4 in accordance with an imaging parameter set at that point. Hence, it is possible to determine whether or not the set parameter is suitable.

Figure 13:
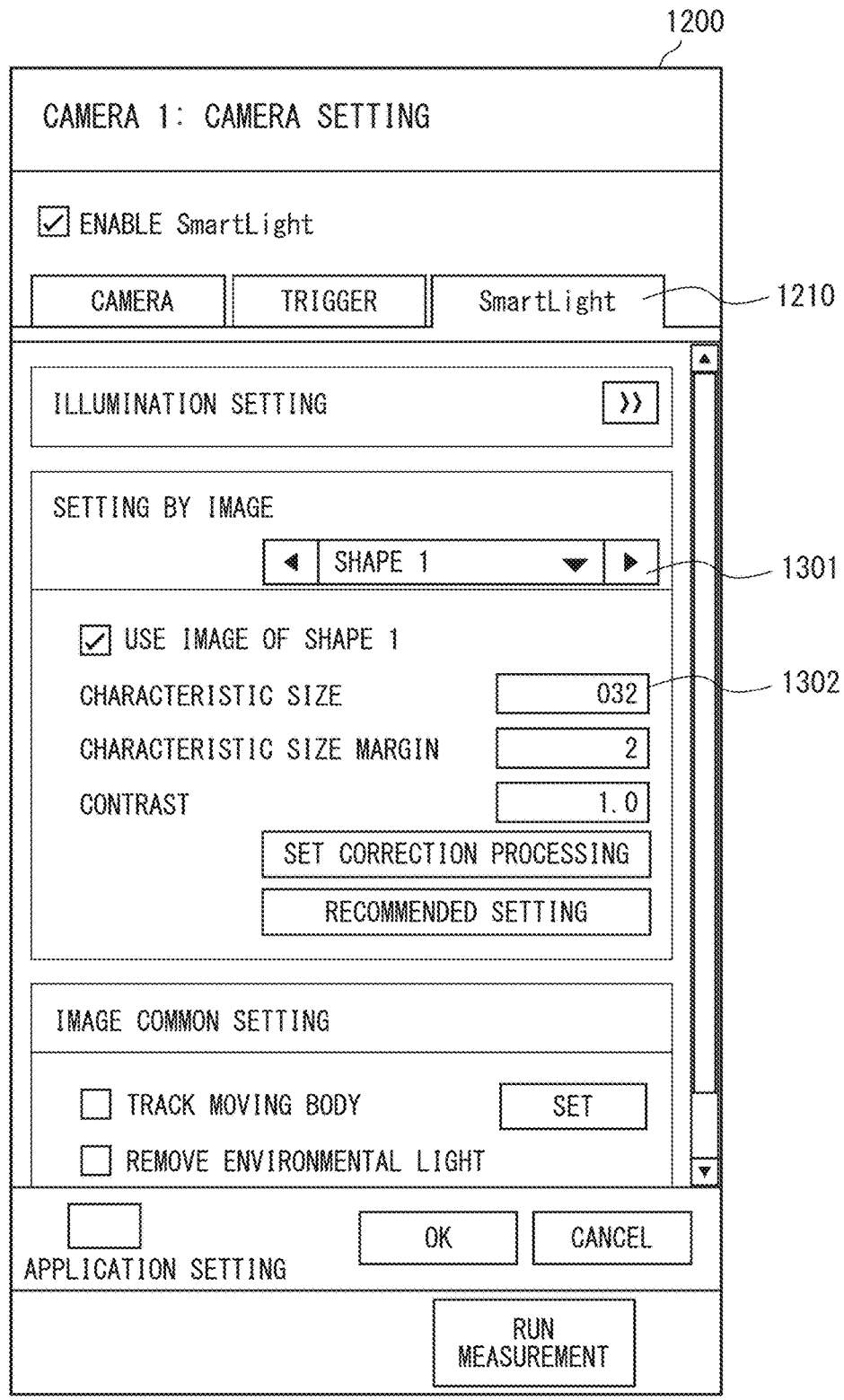
FIG. 13 is a view showing one example of the user interface.

In S902, the UI managing part 814 displays a UI for setting photometric processing on the display part 7, to execute the setting. For example, when detecting that a photometric stereo setting tab 1210 provided in the camera setting UI 1200 is operated, the UI managing part 814 switches the photometric stereo setting tab 1210 to be enabled, as shown in FIG. 13. Switching the photometric stereo setting tab 1210 to be enabled means switching a display state of the photometric stereo setting tab 1210 to a user operable state. The photometric stereo setting tab 1210 includes a pull-down menu 1301 for selecting an image and a characteristic size setting part 1302. In this example, it is assumed that any of three inspection images (shape 1, shape 2, shape 3) with respectively different characteristic sizes can be selected. A characteristic size is set by the characteristic size setting part 1302 for each image selected by the pull-down menu 1301.

A selection part for selecting a lighting pattern may be arranged in the photometric stereo setting tab 1210. Further, a designation part for designating an amount of emission for one illumination may be provided.

Figure 14:
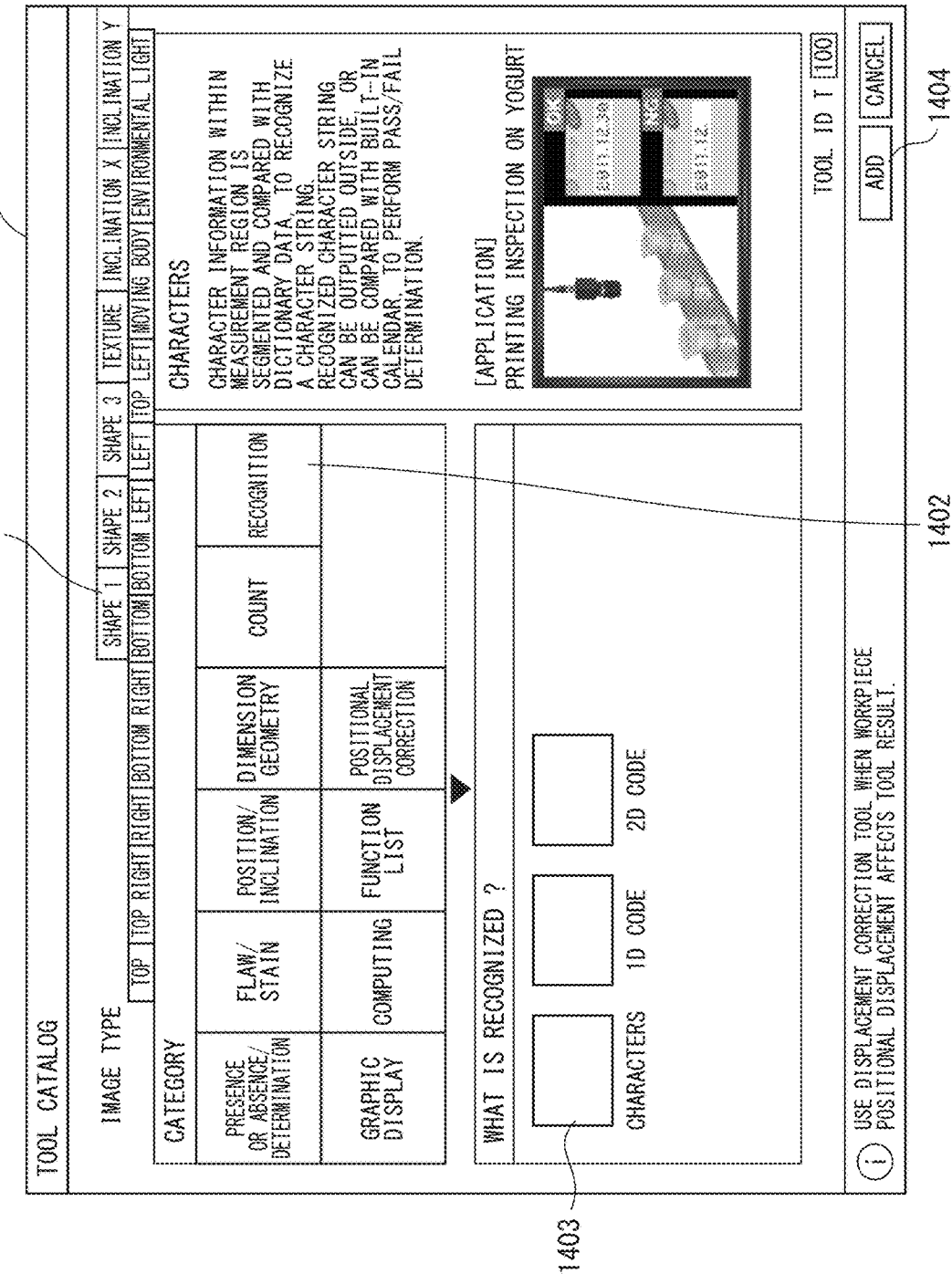
FIG. 14 is a view showing one example of the user interface.
Figure 15:
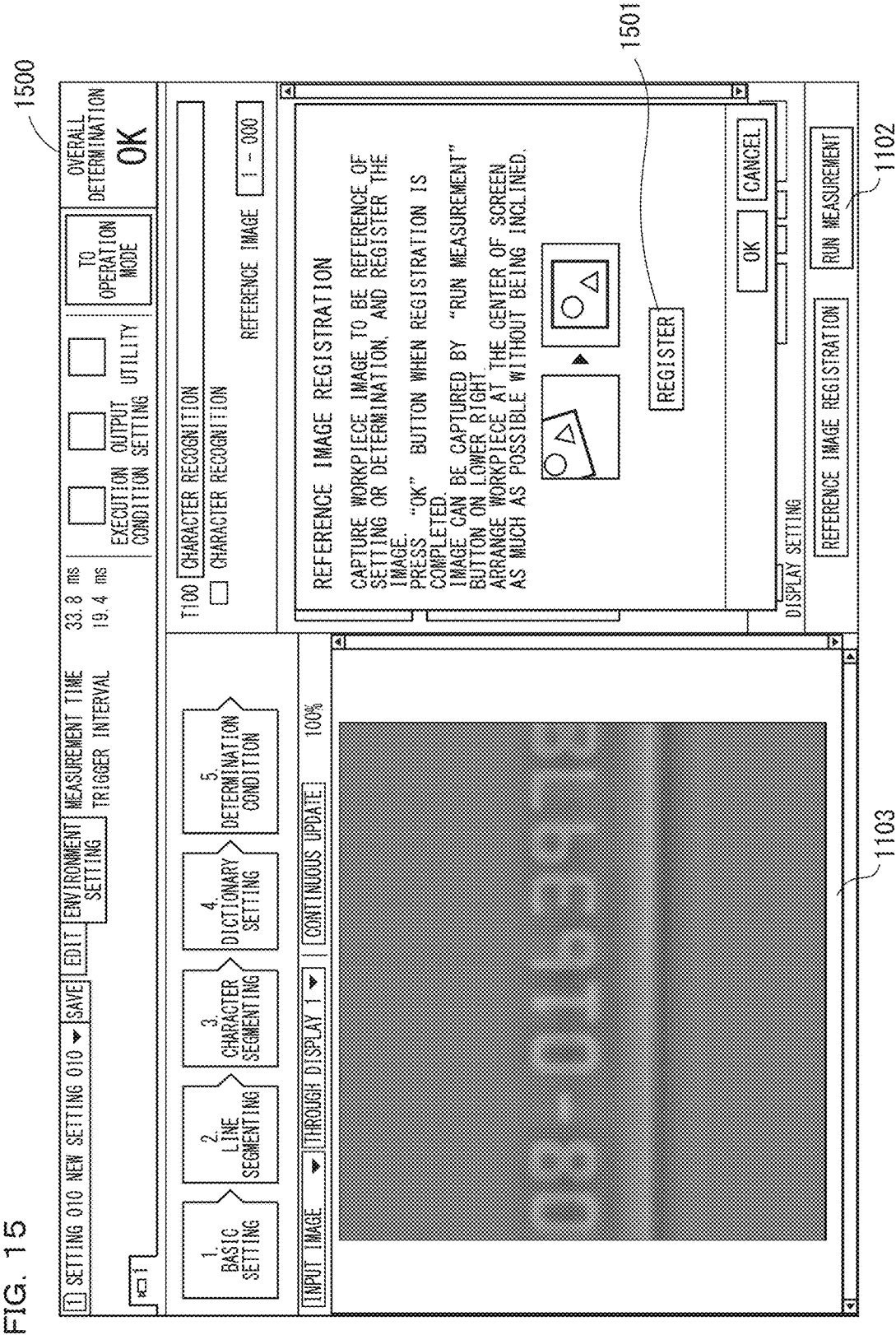
FIG. 15 is a view showing one example of the user interface.

In S903, the UI managing part 814 displays a UI for setting the inspection tool on the display part 7, to execute the setting. FIG. 14 is one example of a UI 1400 for setting the inspection tool. An image selection button 1401 is a button for selecting an inspection image to be used for inspection out of a plurality of inspection images. An inspection category selection button 1402 is a button for selecting a category of a tool to be added as the inspection tool out of a plurality of inspection categories. A recognition target setting button 1403 is a button for selecting one out of a plurality of recognition targets. In this example, "shape 1" is selected as the inspection image, "recognition" is selected as the category, and "character recognition" is selected as the recognition processing. When an addition button 1404 is operated, the UI managing part 814 performs switching to the next UI. FIG. 15 shows a reference image registration UI 1500. The reference image registration UI 1500 is provided with a registration button 1501 in addition to the measurement run button 1102 and the display region 1103 described above. When the registration button 1501 is operated, the UI managing part 814 registers as the reference image an image acquired by the measurement run button 1102 and displayed in the display region 1103. When the registration is completed, the UI managing part 814 performs switching to the next UI.

Figure 16:
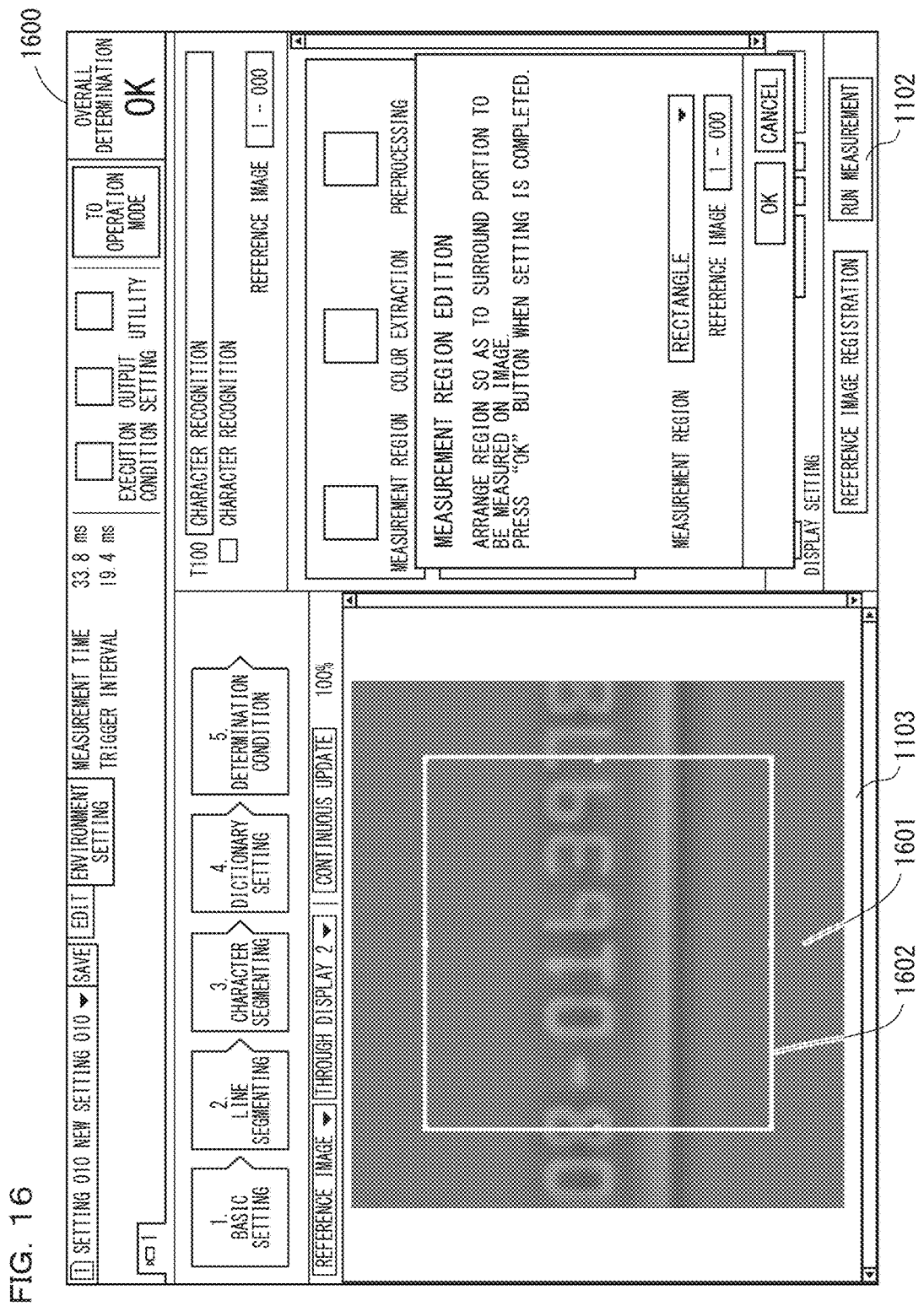
FIG. 16 is a view showing one example of the user interface.

FIG. 16 shows a measurement region setting UI 1600. The display region 1103 of the measurement region setting UI 1600 is provided with a reference image 1601 and a frame 1602 showing a measurement region. The UI managing part 814 changes a position and a size of the frame 1602 in accordance with designation from the input part 6. The user adjusts the position and the size of the frame 1602 in accordance with a position and a size of a portion to be measured in the reference image 1601. The UI managing part 814 further executes character segmenting setting, or dictionary setting for registering a specific example (character image) of a character to be recognized, a character corresponding to the character image, and the like.

Figure 17:
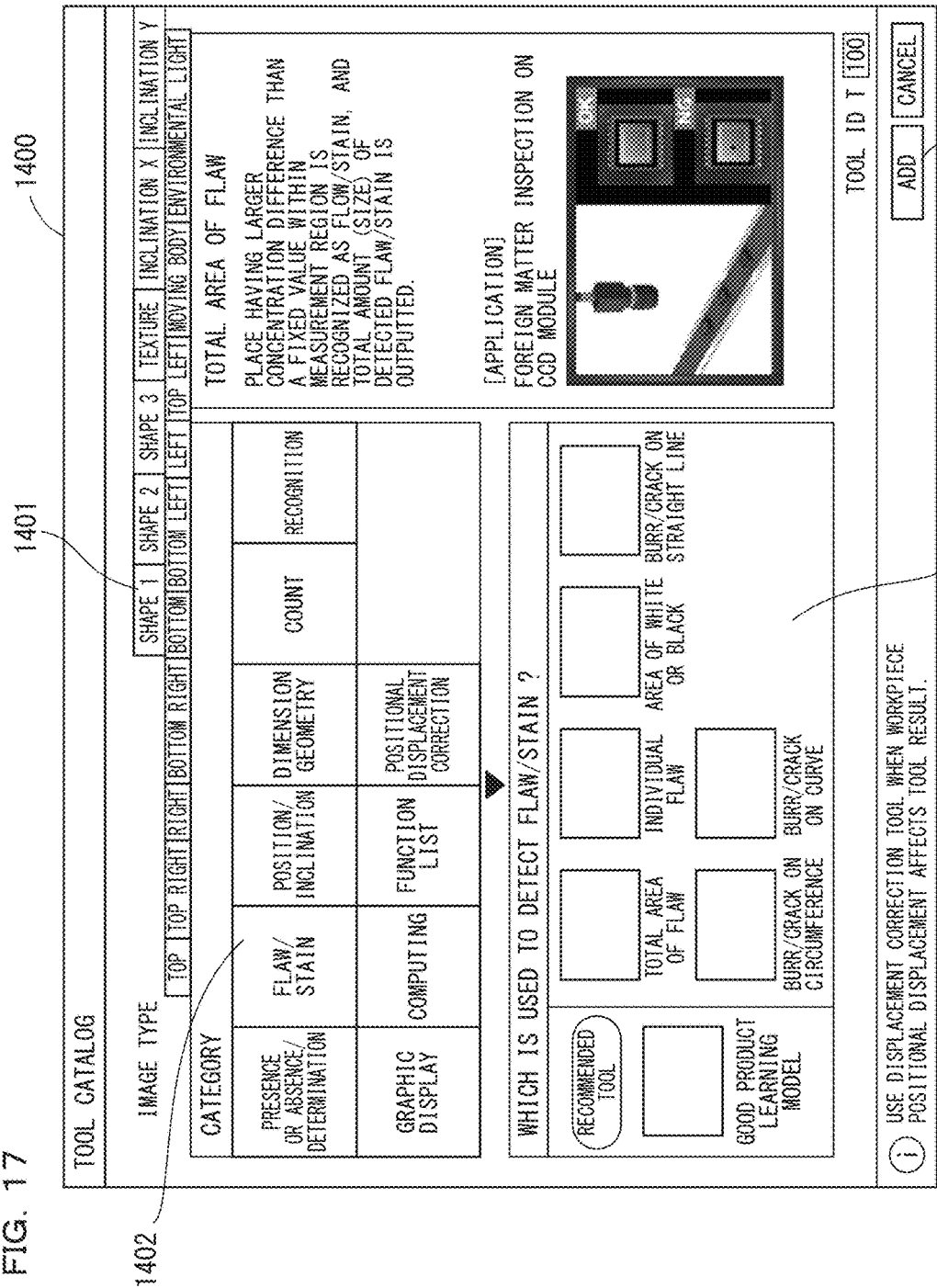
FIG. 17 is a view showing one example of the user interface.

Next, a flaw inspection tool will be described. As shown in FIG. 17, when the flaw inspection is selected by the inspection category selection button 1402, the UI managing part 814 displays an inspection content selection button 1701. In this example, a tool for measuring a total area of a flaw has been selected by the inspection content selection button 1701. When the addition button 1404 is operated, the UI managing part 814 switches the UI.

Figure 18:
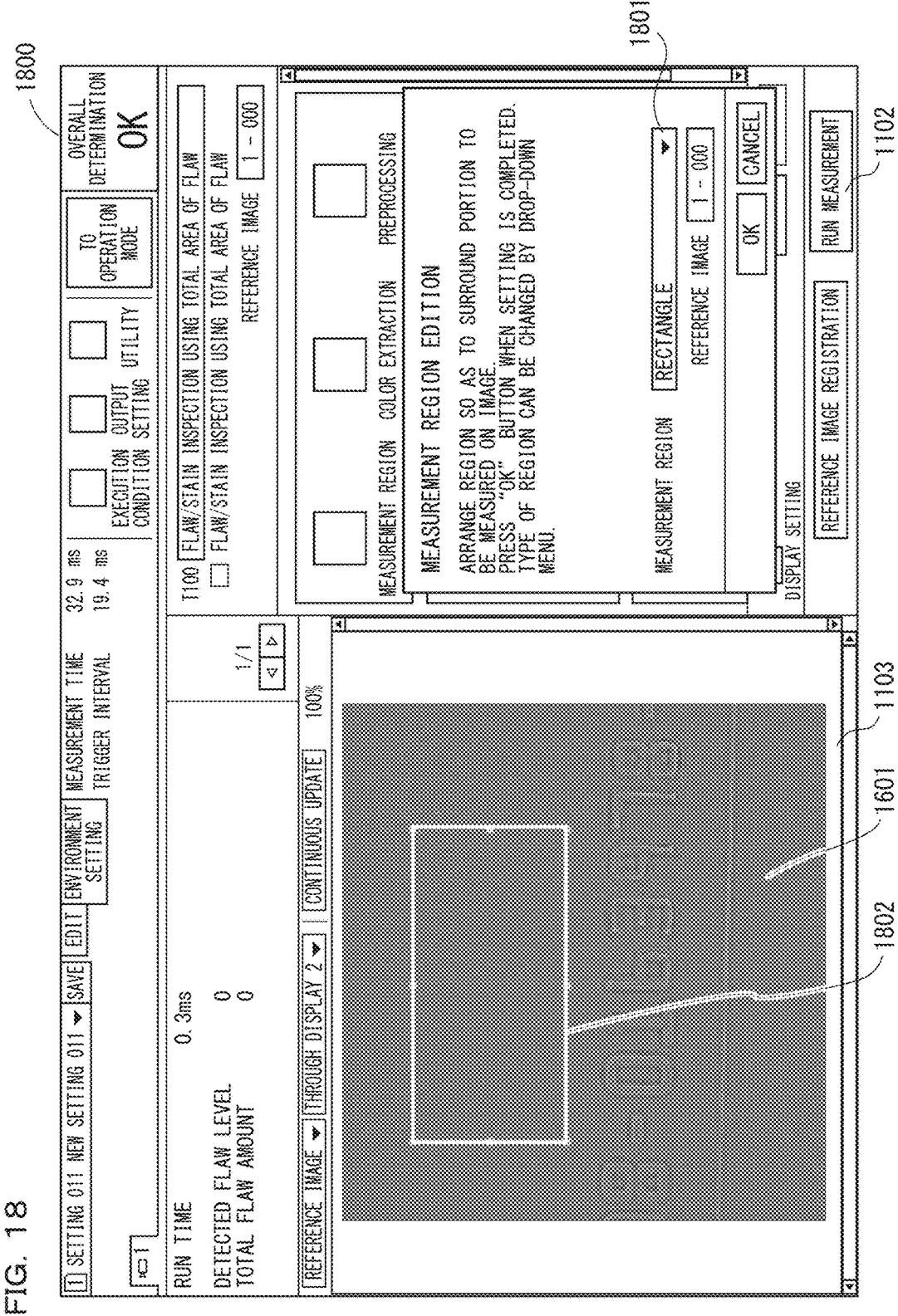
FIG. 18 is a view showing one example of the user interface.

FIG. 18 shows a measurement region setting UI 1800. The measurement region setting UI 1800 is provided with a frame 1802 for showing a measurement region (flaw inspection region). A shape of the frame 1802 is changeable, and for example, any shape out of a plurality of shapes is selected by a pull-down menu 1801 for selecting the shape. The UI managing part 814 renders the frame 1802 having the shape selected by the pull-down menu 1801 to the display region 1103. The UI managing part 814 changes a position and a size of the frame 1802 in accordance with designation from the input part 6.

Figure 19:
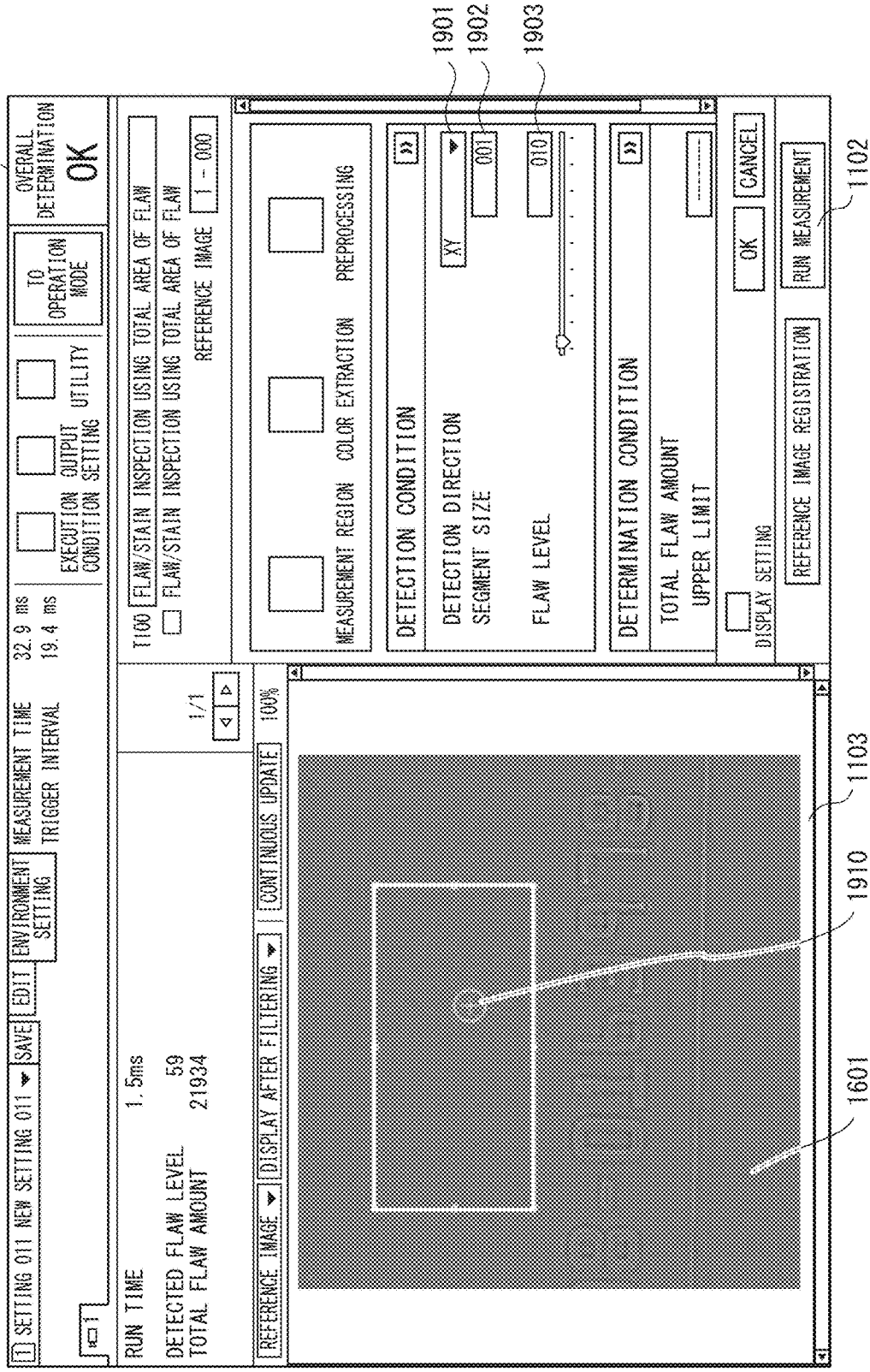
FIG. 19 is a view showing one example of the user interface.

FIG. 19 shows a setting UI 1900 for setting flaw detecting conditions. The setting UI 1900 is provided with a pull-down menu 1901 for selecting a flaw detecting direction, a box 1902 for designating a flaw segment size, and a slider 1903 for designating a flaw level. When the flaw inspection part 831 detects a flaw within the flaw inspection region (frame 1802) based on the flaw detecting conditions set by the setting UI 1900, the UI managing part 814 may display a flaw detection mark 1910 at a position of the flaw. This allows the user to judge whether or not the flaw detection conditions are suitable.

<Inspection Mode>

Figure 20:
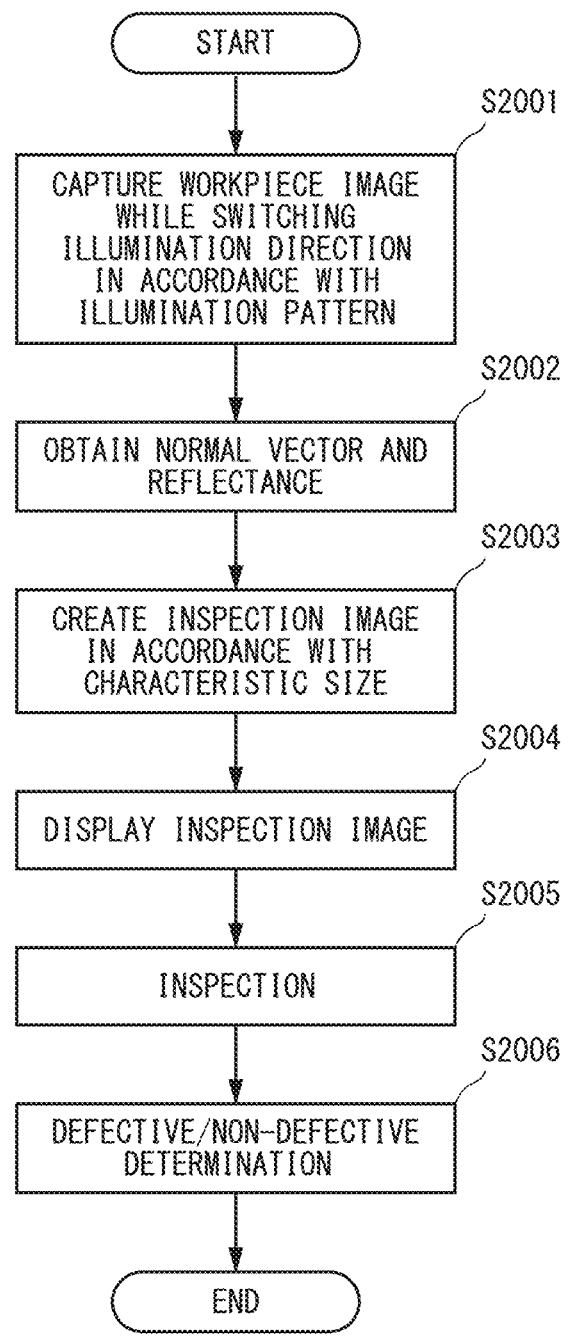
FIG. 20 is a flowchart showing an inspection mode.

FIG. 20 is a flowchart showing the inspection mode. When the start of the inspection mode is designated through the input part 6, the processor 810 switches the operation mode to the inspection mode.

In S2001, the processor 810 captures and acquires an image of the workpiece 2 while switching the illumination direction in accordance with the set lighting pattern. Specifically, the illumination control part 812 specifies the lighting pattern with reference to the setting data held in the storage device 820, and transmits a command for designating the lighting pattern to the illumination controller 802. The imaging control part 813 specifies control parameters (shutter speed, sensitivity, and the like) concerning the camera 4 with reference to the setting data held in the storage device 820, and transmits a command for designating the control parameters to the camera 4. The photometric processing part 811 transmits a trigger signal for designating the start of illumination to the illumination controller 802, and in conjunction with this, the photometric processing part 811 transmits a trigger signal for designating the start of imaging to the camera 4. The illumination controller 802 switches the illumination direction in synchronization with the trigger signal. For example, in accordance with the lighting pattern designated by the command, the illumination controller 802 lights the corresponding light-emitting elements sequentially one by one with respect to the four illumination directions. The illumination controller 802 may hold the corresponding relation between the command and the lighting pattern in a memory or the like. Only one trigger signal may be issued at the start of illumination, or the trigger signal may be issued at switching timing. The camera 4 captures an image of the workpiece 2 in accordance with the control parameters, and transfers the luminance image to the image processing apparatus 5. In such a manner, for example, one luminance image is generated for one illumination direction.

In S2002, the processor 810 obtains the normal vector n and the reflectance ρ from the plurality of luminance images. As described above, the photometric processing part 811 applies Expression 1 to pixel values of the plurality of luminance images, to obtain the normal vector n and the reflectance ρ.

In S2003, the processor 810 generates an inspection image in accordance with the set characteristic size. As described above, the photometric processing part 811 decides the weight W corresponding to the characteristic size from a weight table or the like, and performs the accumulation computing by using Expression 2, to generate an inspection image (inclination image). As thus described, the photometric processing part 811 may generate an inclination image having a pixel value based on the normal vector n of the surface of the workpiece 2 from the plurality of luminance images. When a plurality of characteristic sizes with respectively different values are set, the photometric processing part 811 may generate an inspection image with respect to each of the plurality of characteristic sizes. Further, the photometric processing part 811 may generate a reflectance image or a texture image by the foregoing technique. For example, the photometric processing part 811 may calculate the reflectance ρ of the surface of the workpiece 2 along with the normal vector n of the surface of the workpiece 2 from the plurality of luminance images, to generate a reflectance image having a pixel value based on the reflectance p. Here, an image to be inspected is generated, and generation of an image not to be inspected may be omitted.

In S2004, the processor 810 displays the inspection image on the display part 7. The UI managing part 814 may simultaneously or selectively display on the display part 7 the luminance image, the inclination image, and the reflectance image along with the inspection image. When the images are selectively displayed, the UI managing part 814 may, for example, display the four luminance images by sequentially switching in accordance with switching designation from the input part 6. For example, out of the input part 6, a specific key provided in the console may be allocated as an image switching button.

In S2005, the processor 810 designates the image processing part 830 to execute the inspection. When the inspection is designated, the image processing part 830 activates a previously set inspection tool, to execute the inspection on the inspection image. For example, the flaw inspection part 831 discriminates a flaw level in accordance with the set measurement region and detection conditions, and transmits a result of the inspection (flaw level) to the determination part 840. Note that the flaw inspection part 831 may execute a pattern search by using the foregoing reference image and set an inspection region, to execute the inspection in the inspection region. Further, the OCR part 832 performs character recognition processing on the inspection image in accordance with a previously set character recognition setting, and transmits a result of the character recognition to the determination part 840. The OCR part 832 may also execute a pattern search by using the foregoing reference image and set an inspection region (character recognition region), to execute inspection in the inspection region.

In S2006, the determination part 840 of the processor 810 compares the inspection result and a determination threshold, to determine whether or not the workpiece 2 is a non-defective product. For example, in a case where a setting has been performed so as to execute both the flaw inspection and the OCR, the determination part 840 determines the workpiece 2 as a non-defective product when both of the result of the inspection by the flaw inspection part 831 and the result of the character recognition by the OCR part 832 are at passing levels.

<Image Saving Setting>

Figure 21:
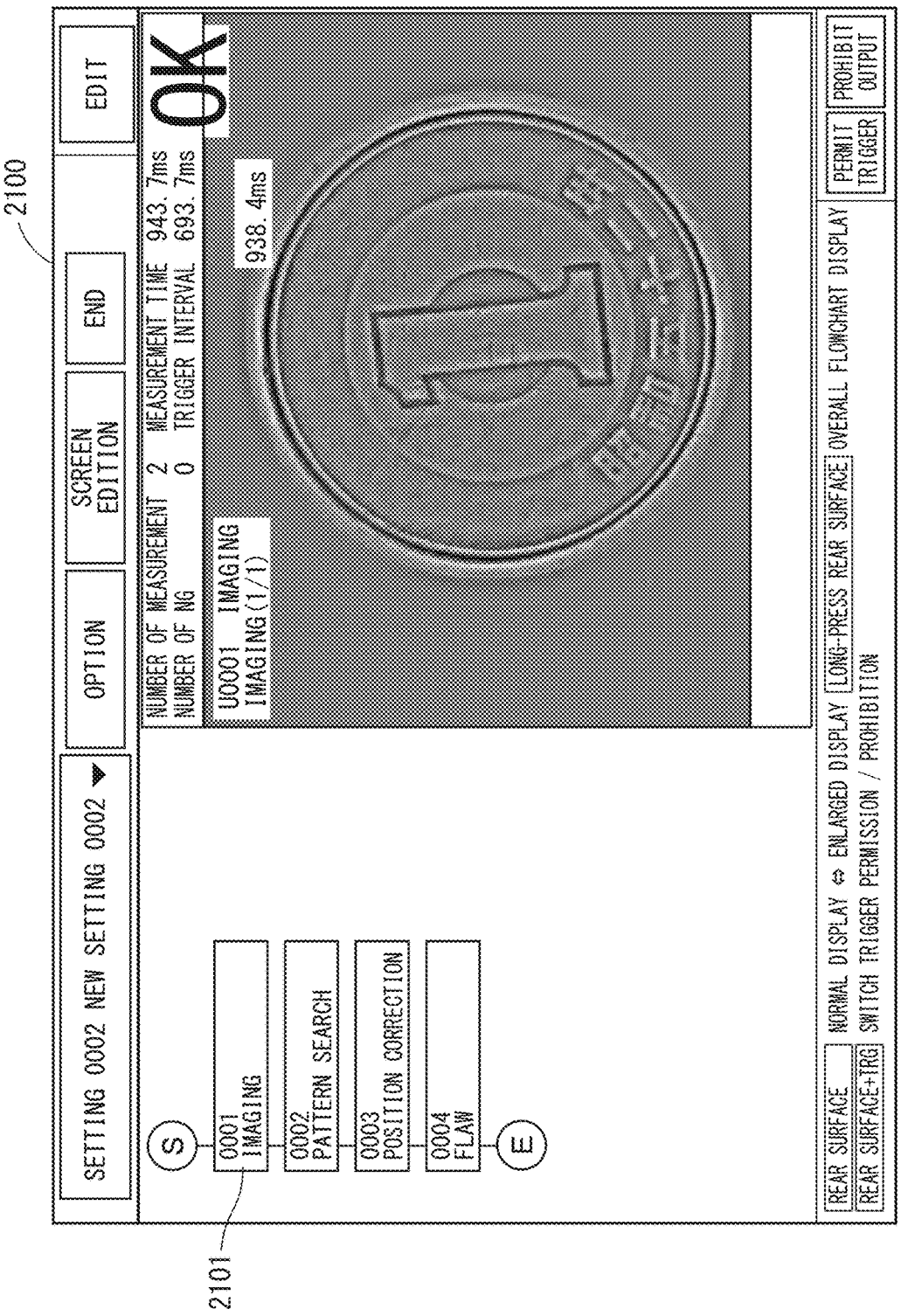
FIG. 21 is a view showing one example of the user interface.

FIG. 21 shows one example of a UI 2100 for setting an inspection flow. The UI managing part 814 displays the UI 2100 on the display part 7, and sets a plurality of steps to be performed from the start to the end of the inspection flow in accordance with designation inputted from the input part 6. In this example, an imaging step, a pattern search step, a position correcting step and a flaw inspecting step are added to the inspection flow. For example, when the end of the inspection flow is designated through the input part 6, the UI managing part 814 may perform such a setting as to store an inspection history at the end. The inspection history is an inspection result, an image used in the inspection, and the like.

At the time of adding each step, the UI managing part 814 may accept selection of an image to be used in each step through the input part 6. For example, through the input part 6, the user may designate four luminance images with four different illumination directions, an inclination image, a reflectance image, or the like as an acquirement target for the imaging step. The user may designate any of luminance images (all-directional illumination image, etc.) as a search target for the pattern search step. The user may designate an inspection image generated from the inclination image as an inspection target for the flaw inspecting step. In the present embodiment, a plurality of shape images and a reflection image generated from the plurality of luminance images captured in the imaging step can be outputted in the later-stage inspection step, whereby the user can apply a plurality of inspection images generated from the common imaging step to a variety of inspections corresponding to characteristics of each image.

Figure 22:
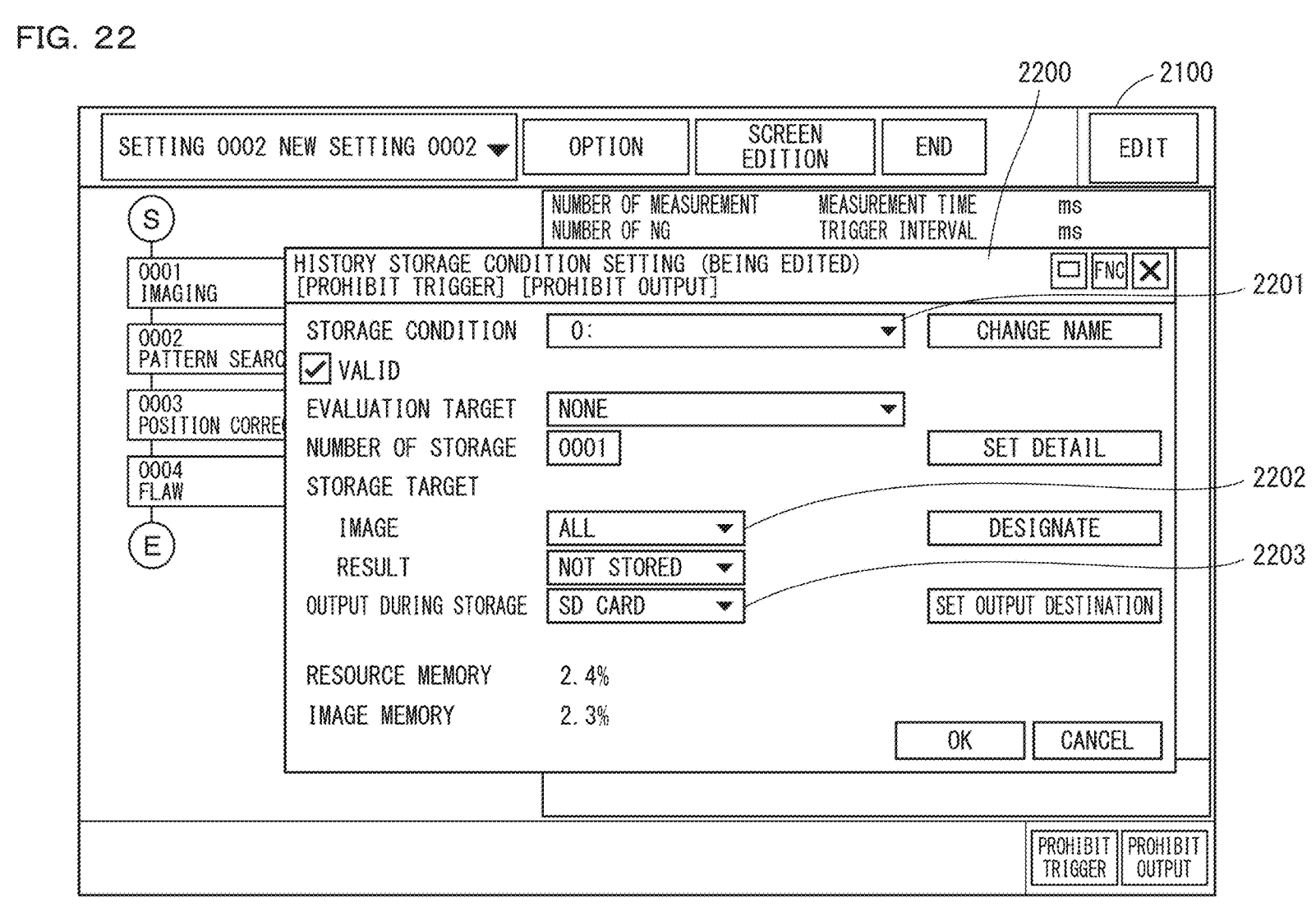

FIG. 22 shows one example of a UI 2200 for setting a condition for storing histories. A setting part 2201 for setting identification information for identifying the storage condition is a pull-down menu for selecting identification information to be set from a plurality of pieces of identification information. In this example, in the setting part 2201, a storage condition for identification information of "0:" is selected. Examples of the storage condition includes a condition that images are stored only when an inspection result shows that the workpiece is not a non-defective product, and a condition that images are constantly stored for each workpiece without depending on the inspection result. Here, the processor 810 activates the condition setting part 819 when detecting that a detail setting button or the like is pressed. The condition setting part 819 may, for example, set one of a mode for constantly saving or outputting an image, and a mode for saving or outputting an image when the determination part 840 determines that an inspection target is not a non-defective product. An image selection part 2202 selects an image that is saved when the storage condition is satisfied. Here, "all" or "designate" can be selected by the image selection part 2202. A saving destination selection part 2203 is a pull-down menu for selecting an image saving destination (e.g., a portable medium such as an internal memory or a memory card, or network storage such as an FTP server).

Figure 23:
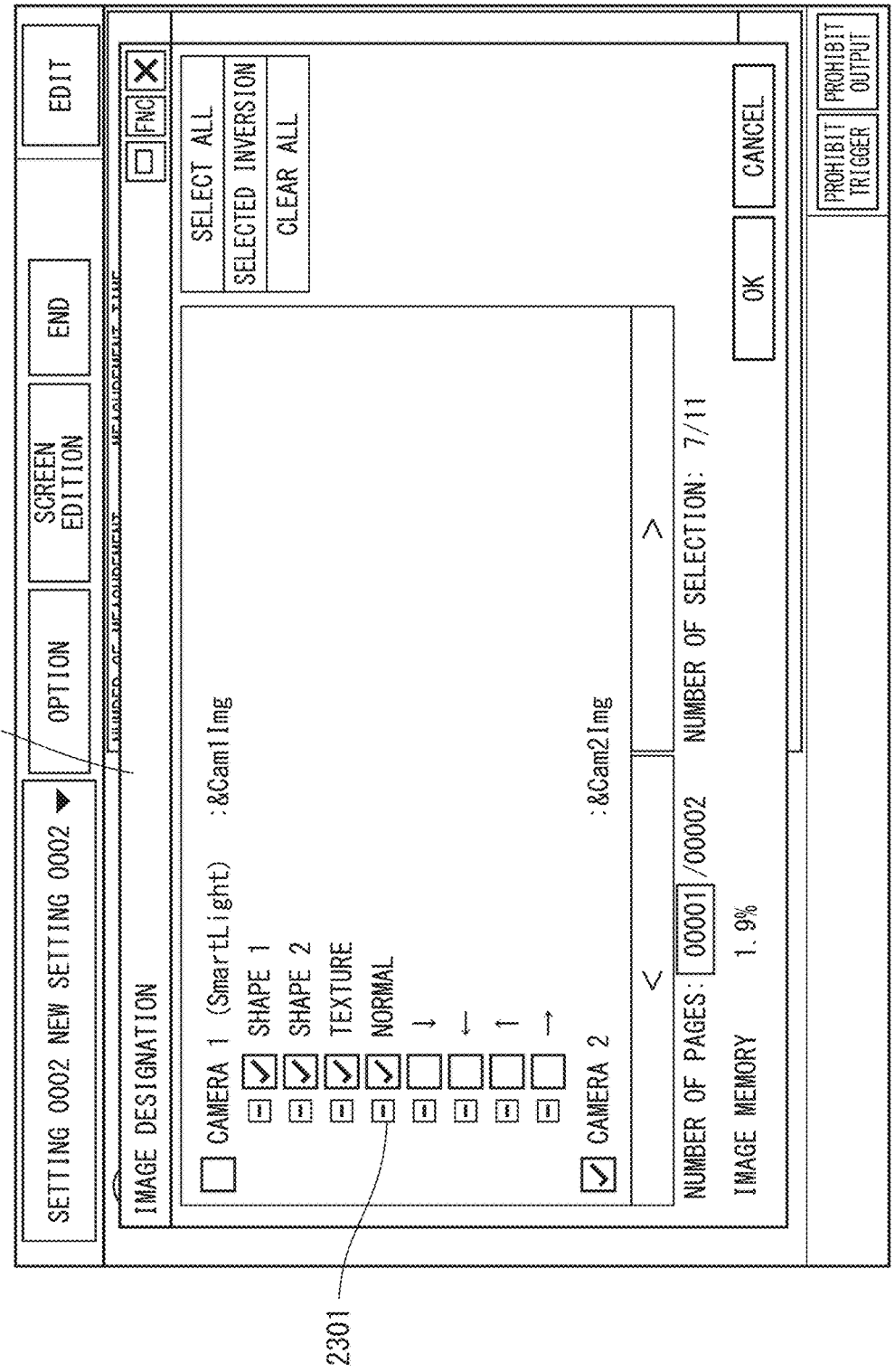
FIG. 23 is a view showing one example of the user interface.

FIG. 23 shows one example of a UI 2300 that the UI managing part 814 displays on the display part 7 when "designate" is selected in the image selection part 2202. In this example, there is provided a check box 2301 for selecting an image to be actually saved out of all types of images handled in the inspection flow. "Shape 1" and "shape 2" are inspection images (inclination images) with different characteristic sizes. "Texture" is a reflectance image. "Normal" is an image acquired by all-directional illumination. Four arrows are icons indicating illumination directions. That is, four luminance images with four different illumination directions are discriminated by the arrow marks. An image whose check box is checked is set as an image to be saved.

Incidentally, the processor 810 may be provided with a judgment section for judging whether or not a condition for saving or outputting an image is satisfied after the determination part 840 completes the determination. That is, in the end part of the inspection flow, the processor 810 may judge whether or not the storage condition or the output condition set by the condition setting part 819 is satisfied.

Figure 24:
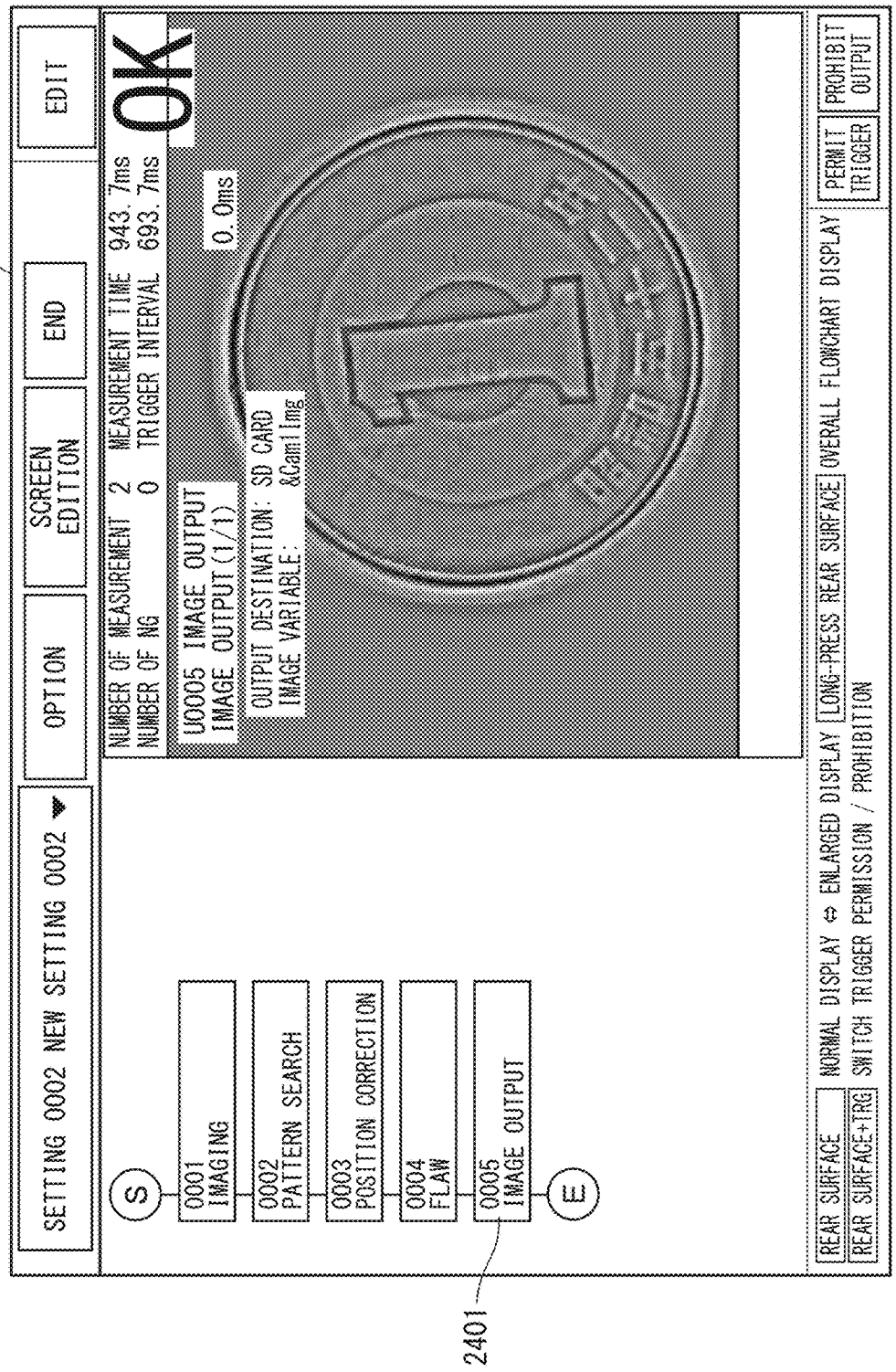
FIG. 24 is a view showing one example of the user interface.

FIG. 24 shows an example of adding an image outputting step 2401 to the inspection flow. In the foregoing example, the setting has been performed so as to output an image at the end of the inspection flow, but in this example, the UI managing part 814 sets the image outputting step 2401 at an arbitrary position of the inspection flow in accordance with the user's designation inputted from the input part 6. In such a manner, the processor 810 may judge whether or not the condition for saving or outputting an image is satisfied in the image outputting step 2401 located before the determination part 840 completes the determination. The storage setting and the like related to the image outputting step 2401 may be similar to those described using FIGS. 21 to 23, or may be different.

Figure 25:
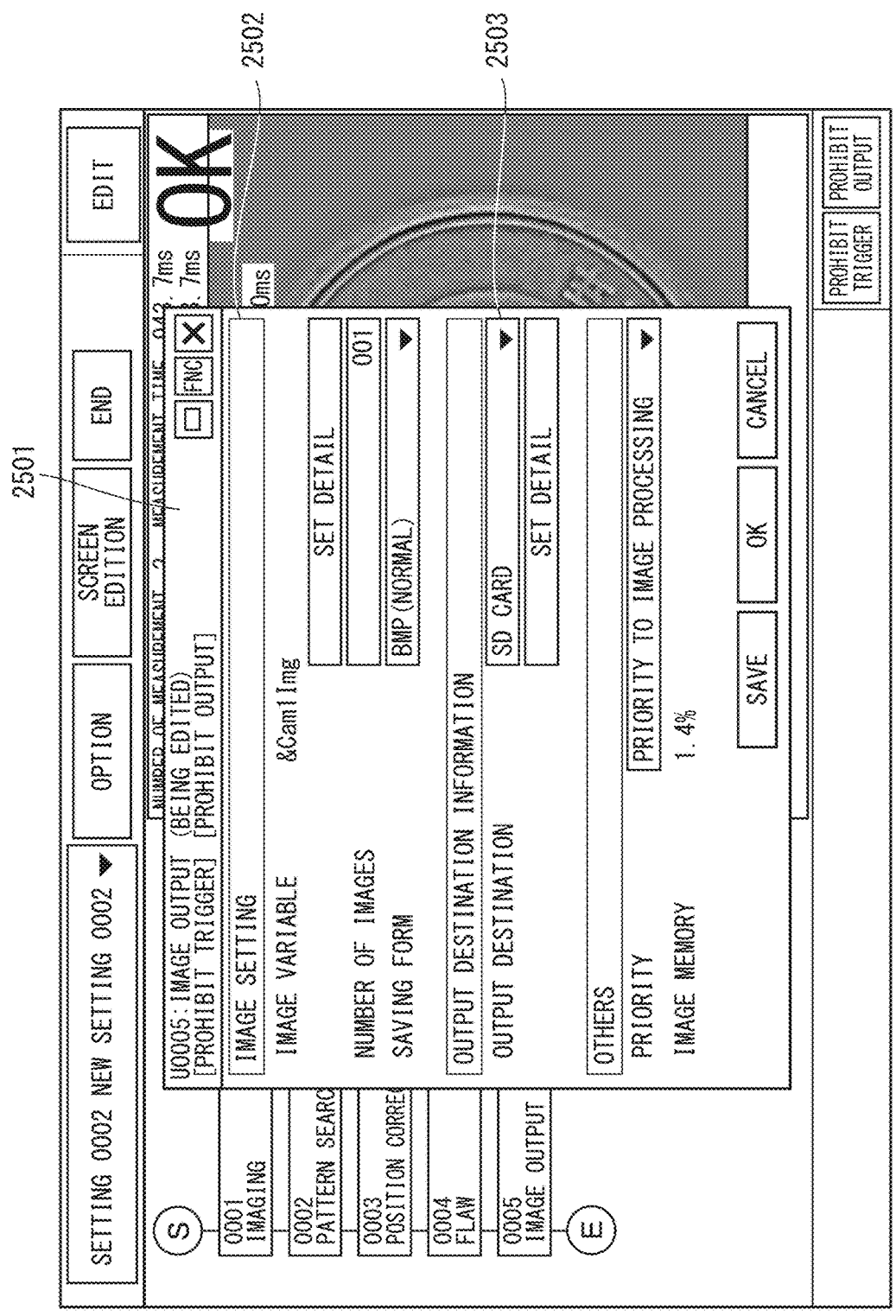
FIG. 25 is a view showing one example of the user interface.

FIG. 25 shows a different example of a UI related to the storage setting (output setting). In a state where the image outputting step 2401 has been selected by the input part 6, when designation to start a setting is further inputted by the input part 6, the UI managing part 814 displays a UI 2501. An image variable 2502 functions as an image selection part for selecting an image to be outputted, and in this example, an image to be outputted is designated by the image variable that is added to each step in the inspection flow. That is, the image to be outputted can be selected for each step. In the UI 2501, the number of outputted images, an image form, and the like may be set. An output destination selection part 2503 is a pull-down menu for selecting an image outputting destination (e.g., a portable storage medium such as an internal memory or a memory card, or network storage such as an FTP server).

Figure 26:
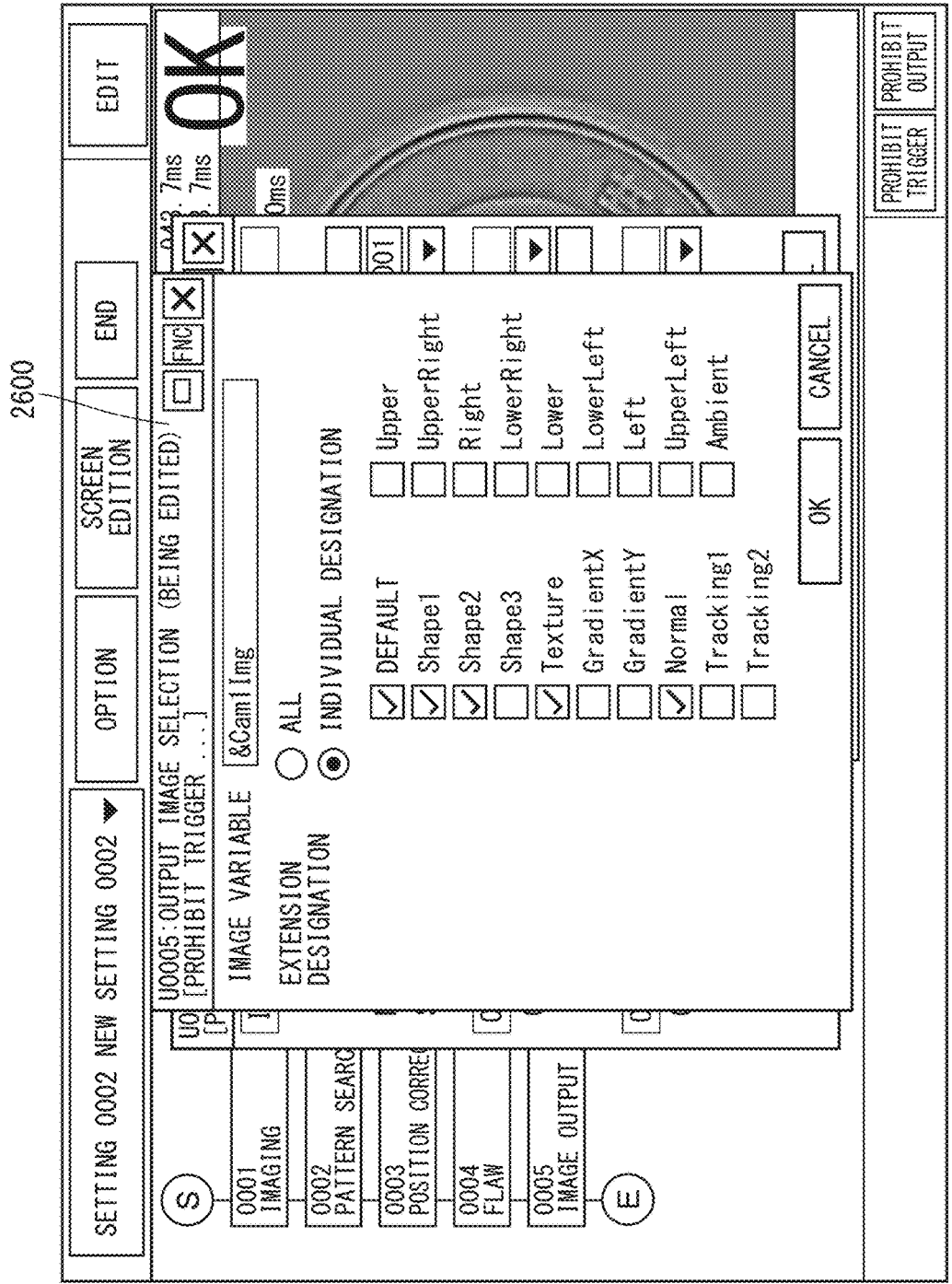
FIG. 26 is a view showing one example of the user interface.

FIG. 26 is one example of a UI 2600 for selecting an image. When a detail setting button is pressed down in the UI 2501, the UI managing part 814 displays a UI 2600. The UI 2600 is provided with a radio button for selecting whether to save all images or to individually designate the images, check boxes for individually selecting the images, and the like. In this example, since the individual setting is selected by the radio button, check boxes are enabled, and several images are selected by the check boxes. In such a manner, an image to be saved or outputted may be selected out of a plurality of luminance images, an inspection image, an all-directional illumination image, and a synthesized luminance image obtained by synthesizing the plurality of luminance images. Further, the UI 2600 may be configured so as to select an image, which is to be saved or outputted, out of a plurality of inspection images with respectively different characteristic sizes. Moreover, the UI 2600 may be configured such that an image to be saved or outputted can be selected out of a plurality of luminance images, an inspection image, and a reflectance image whose pixel value is a reflectance of the surface of the inspection target.

<Configuration of Illumination Apparatus>

Figure 27A:
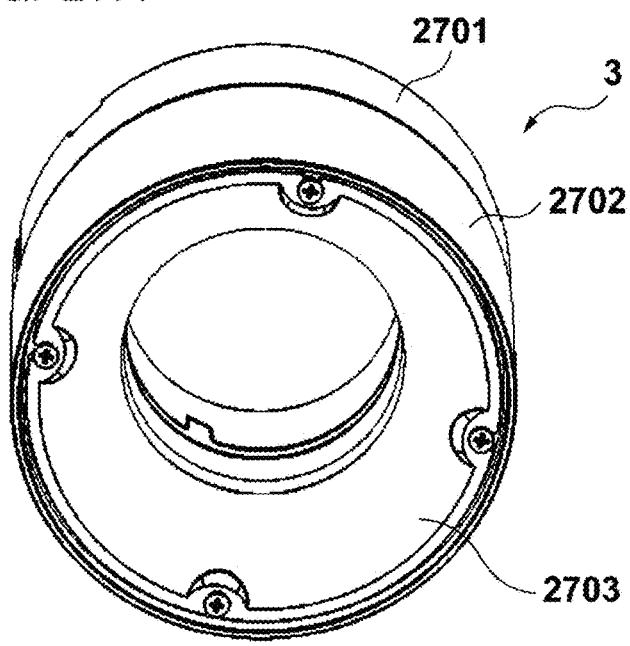
FIGS. 27A to 27D are views for describing a structure of an illumination apparatus.
Figure 27B:
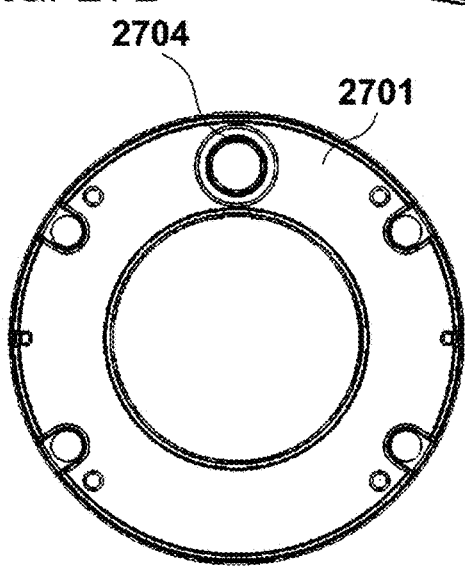
Figure 27C:
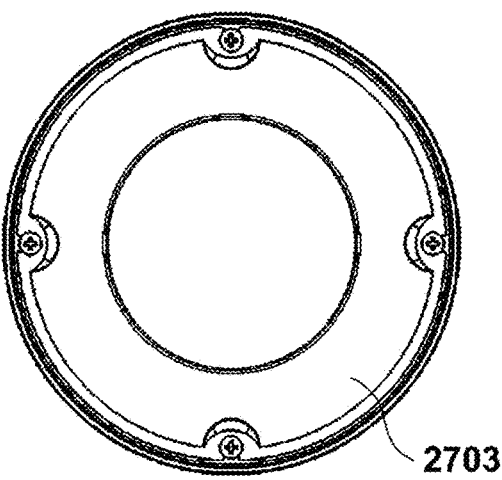
Figure 27D:
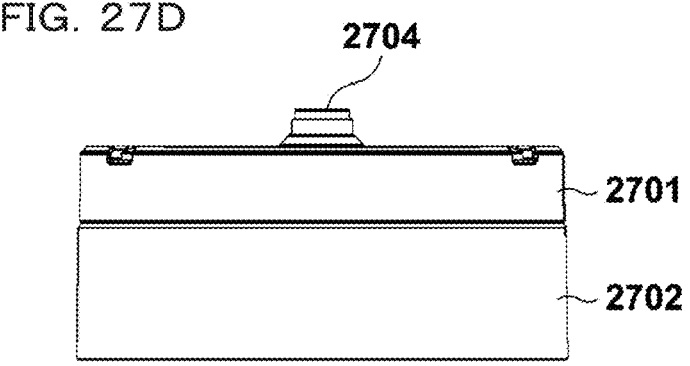

FIG. 27A is a perspective view of the illumination apparatus 3. FIG. 27B is a top view of the illumination apparatus 3. FIG. 27C is a bottom view of the illumination apparatus 3. FIG. 27D is a side view of the illumination apparatus 3. The housing of the illumination apparatus 3 has an upper case 2701 and a lower case 2702. A lower part of the lower case 2702 is arranged with a light diffusion member 2703 for diffusing light emitted from each of a plurality of light sources (light-emitting elements such as LEDs). As shown in FIGS. 27A and 27C, the light diffusion member 2703 forms an annular shape as do the upper case 2701 and the lower case 2702. As shown in FIGS. 27B and 27D, the top surface of the upper case 2701 is provided with a connector 2704. The connector 2704 is connected with a cable for communicating the illumination controller 802 stored in the illumination apparatus 3 and the image processing apparatus 5.

Figure 28A:
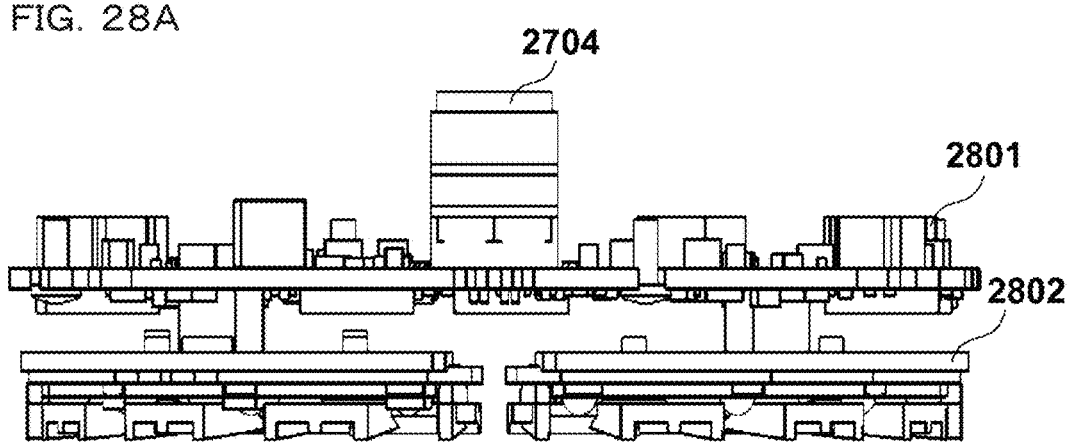
FIGS. 28A to 28E are views for describing the structure of the illumination apparatus.
Figure 28B:
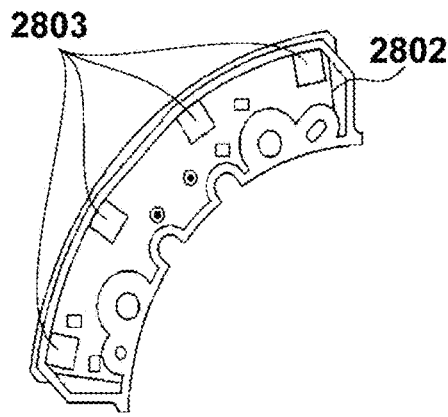
Figure 28C:
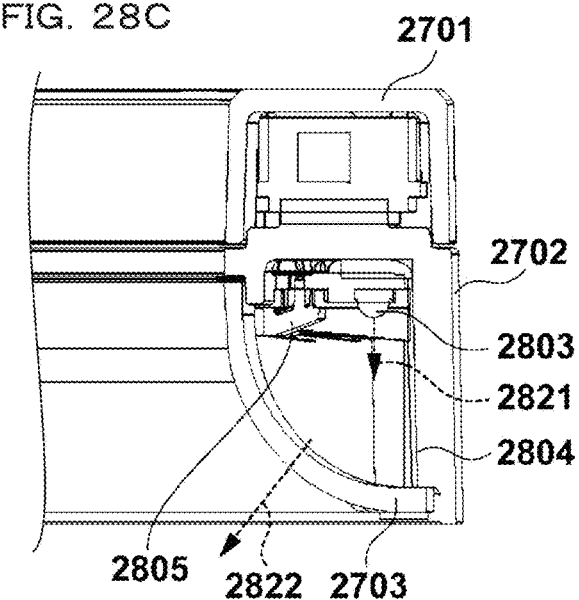
Figure 28D:
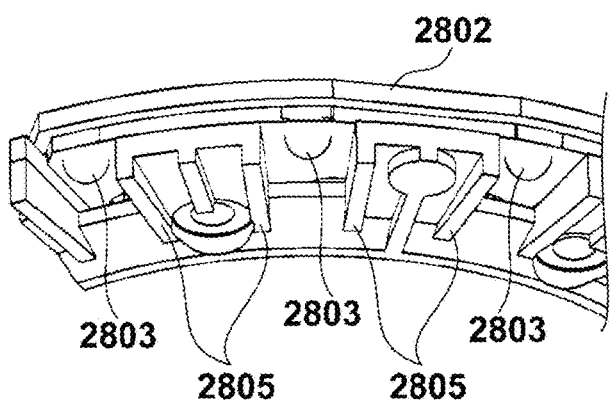
Figure 28E:
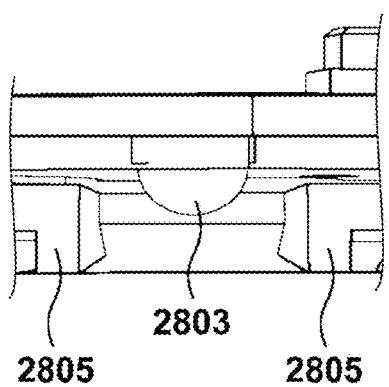

FIG. 28A is a side view showing a control substrate 2801 and an LED substrate 2802 which are stored in the illumination apparatus 3. The control substrate 2801 is one example of a second substrate on which the lighting control part is mounted. The LED substrate 2802 is one example of a first substrate on which a plurality of light sources are mounted. FIG. 28B is a top view of the LED substrate 2802. FIG. 28C is an enlarged sectional view of the vicinity of an LED 2803 out of the illumination apparatus 3. FIG. 28D is a bottom view of the LED substrate 2802. FIG. 28E is an enlarged side view of the vicinity of the LED 2803 out of the LED substrate 2802.

The control substrate 2801 is arranged with the illumination controller 802 and the connector 2704. Light-emitting elements such as LEDs constituting the light source group 801 are mounted on the LED substrate 2802. As shown in FIG. 28B, four LED substrates 2802 are provided in the present embodiment. It is assumed that the four respective LED substrates 2802 are arranged with four LEDs 2803. Thereby, the light source group 801 is made up of 16 light-emitting elements. As shown in FIGS. 28C, 28D and 28E, a shading member 2805 is arranged between two adjacent LEDs 2803 out of the plurality of LEDs 2803. When a large number of LEDs 2803 are densely arranged, illumination light emitted from each of two adjacent LEDs 2803 passes through the same region of the light diffusion member 2703 in some case. In this case, both in a case where one LED 2803 is not lighted and the other LED 2803 is lighted in accordance with a lighting pattern and in a case where one LED 2803 is lighted and the other LED 2803 is not lighted, the surface of the workpiece 2 is irradiated with the same amount of illumination light from the same illumination direction. This makes it difficult to generate an inspection image with high accuracy. Therefore, by arranging the shading member 2805 between two adjacent LEDs 2803, the balance of uniformity of light amounts and independency of the light sources are kept as to the two adjacent LEDs 2803. As shown in FIG. 28C, a light injecting direction 2821 of the LED 2803 does not match with a main illumination direction 2822. Therefore, a reflecting mirror 2804 is arranged, to deviate light, injected from the LED 2803, in a direction to the light diffusion member 2703. This allows the workpiece 2 to be efficiently irradiated with light emitted by the LEDs 2803. The injecting direction 2821 and a reflecting direction of the reflecting mirror 2804 are mostly orthogonal to each other in this example, and this is because a sectional shape of the light diffusion member 2703 forms an arc (FIG. 28C), and an angle (central angle) concerning an arc is about 90 degrees. As thus described, making the central angle large facilitates irradiating the surface of the workpiece 2 with almost uniform parallel light even when the illumination apparatus 3 is brought away from or close to the surface of the workpiece 2.

<Circuit Configuration of Illumination Apparatus>

Figure 29:
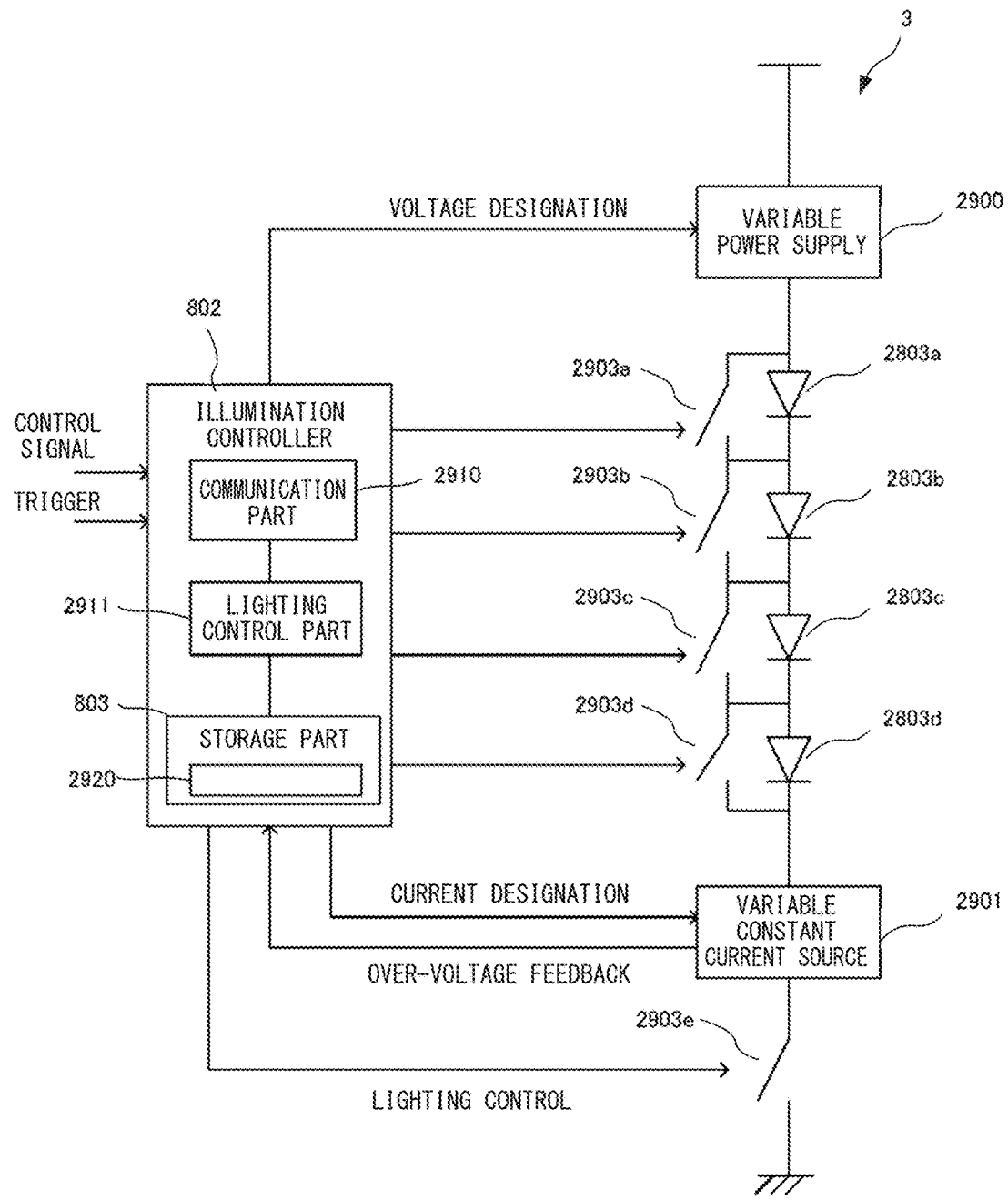
FIG. 29 is a block diagram concerning lighting control.

FIG. 29 shows one example of a circuit configuration of the illumination apparatus 3. In this example, one group is shown out of four LED groups constituting the light source group 801. Four LED 2803a to LED 2803d are connected in series. A variable power source 2900 with a variable voltage generates and outputs a voltage with a voltage value (e.g., 2 V to 20 V) designated by the illumination controller 802. The variable constant current source 2901 adjusts a current flowing to an LED group so as to become a current value (e.g., 0 A to 1 A) designated by the illumination controller 802. Adopting such a current control system facilitates realizing control of light with high linearity. Further, the variable constant current source 2901 detects a value of a voltage being applied to the variable constant current source 2901, feeds back the voltage to the illumination controller 802, and protects the variable constant current source 2901 from an overvoltage. Switches 2903a to 2903d are connected in parallel to the respective LED 2803a to LED 2803d. A lighting control part 2911 of the illumination controller 802 can individually open and close these switches 2903a to 2903d, to individually switch lighting and non-lighting of each of the LED 2803a to LED 2803d. In such a manner, connecting the switches 2903a to 2903d in parallel to the respective LED 2803a to LED 2803d allows individual lighting in which any one of the LED 2803a to LED 2803d is lighted or lighting all of the LED 2803a to LED 2803d. This is useful for realizing a variety of lighting. Note that the lighting control part 2911 switches on/off of a main switch 2903e inserted between the variable constant current source 2901 and the ground, to execute lighting control by an LED group unit. A communication part 2910 receives a control signal for designating a lighting pattern or a trigger signal for designating start of lighting from the illumination control part 812 of the image processing apparatus 5, and pass the signal to the lighting control part 2911. The lighting control part 2911 reads from the storage part 803 lighting pattern data 2920 corresponding to a control signal, and controls the switches 2903a to 2903d in accordance with the lighting pattern data 2920. The lighting pattern data 2920 may include identification information of light sources that are simultaneously lighted at one lighting timing out of a plurality of light sources, and information indicating an order of lighting a plurality of light sources. For example, 16 LEDs can be distinguished by means of 16-bit identification information. The lighting pattern data 2920 may include information indicating the number (dividing number) of illumination directions. The number of illumination directions is basically four, but may be eight. The lighting pattern data 2920 may include information indicating the number of lighted elements (number of light sources that are simultaneously lighted at one lighting timing). For example, in the case of a basic number of lighted elements, four LEDs are lighted. In contrast, in the case of one half of the number of lighted elements, two LEDs are lighted, and in the case of one quarter of the number of lighted elements, one LED is lighted. The lighting pattern data 2920 may include information designating the timing for lighting all the LEDs. For example, entire lighting may be designated before execution of lighting in accordance with the photometric stereo method, or entire lighting may be designated after execution of lighting in accordance with the photometric stereo method. Further, the lighting pattern data 2920 may include information indicating a lighting starting position. For example, the lighting pattern data 2920 may include identification information indicating an LED to be firstly lighted out of the 16 LEDs. In this case, an LED to be lighted is changed in accordance with illumination directions clockwise from the LED to be firstly lighted. The lighting pattern data 2920 may be made up of information indicating the number of lighting times (1 to 16 times) in one lighting cycle and identification information (0 x 000 to 0 x FFFF) of the LED to be lighted. The lighting pattern data 2920 may include an illumination light amount and lighting time (exposure time) per LED, and the interval time indicating a lighting interval. As thus described, the lighting control part 2911 turns on a plurality of LEDs 2803 in accordance with the lighting pattern data 2920 stored in the storage part 803 and specified by a control signal received via the signal line 8. Hence, the number of signal lines can be significantly reduced compared to the case of arranging the signal line 8 for each LED.

Figure 30:
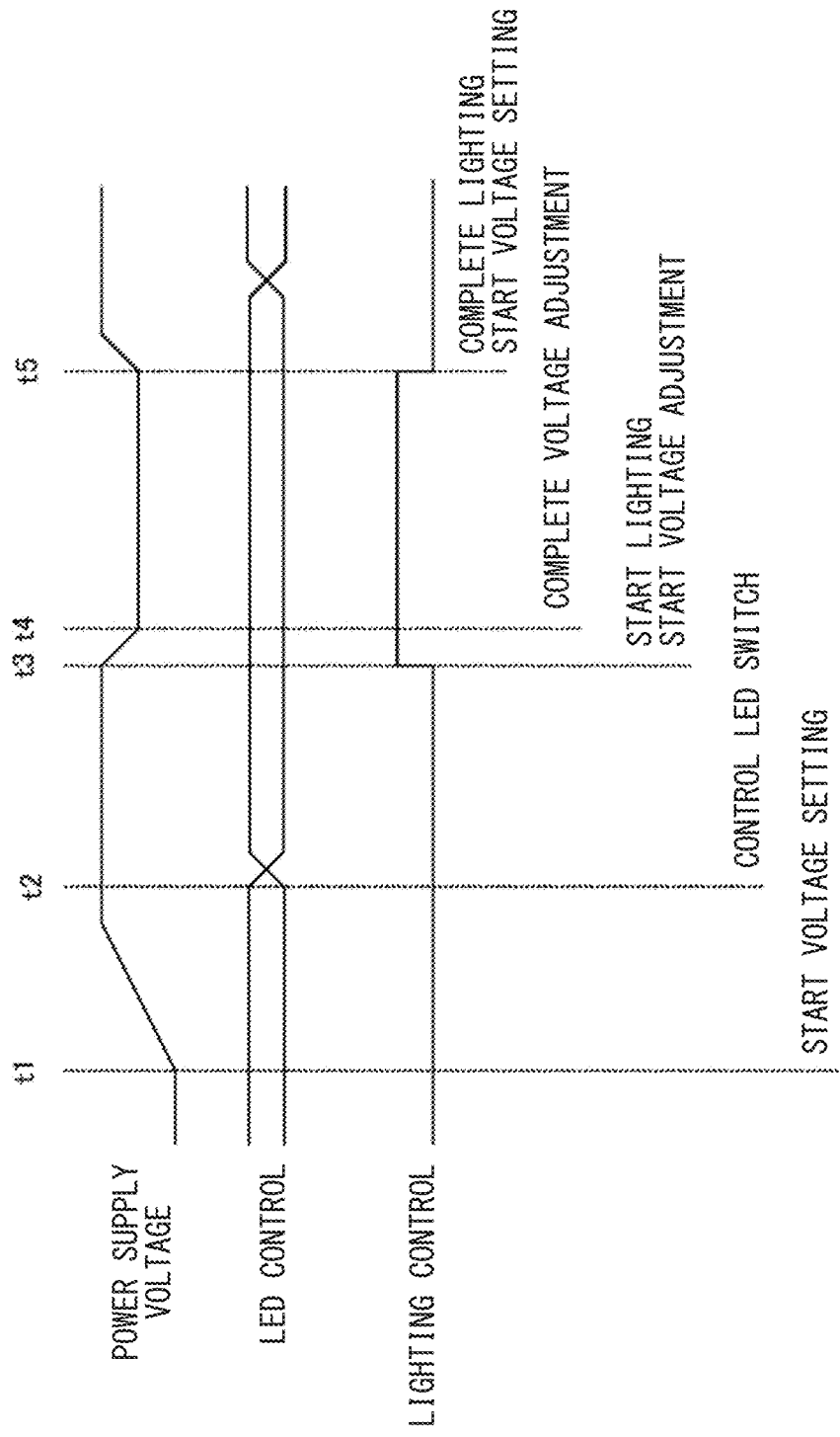
FIG. 30 is a diagram showing a timing sequence concerning lighting control.

FIG. 30 is a diagram showing a timing sequence for lighting control. When receiving a control signal at time t1, the lighting control part 2911 decides a voltage value in accordance with a lighting pattern and sets the voltage value in the variable power source 2900. Since it takes time for a voltage outputted by the variable power source 2900 to be stabilized at a target voltage, a voltage setting is first executed. This leads to improvement in responsiveness of lighting.

At time t2, the lighting control part 2911 individually sets on/off of the switches 2903a to 2903d in accordance with a lighting pattern. That is, the switch connected in parallel to the LED being designated to be lighted by the lighting pattern is switched on, and the switch connected in parallel to the LED being designated not to be lighted by the lighting pattern is switched off.

When receiving a trigger signal at time t3, the lighting control part 2911 switches on the main switch 2903e. Thereby, the LED is lighted in accordance with the lighting pattern. Note that the lighting control part 2911 adjusts a voltage to be applied to the LED group in accordance with the number of lighted LEDs (in accordance with overvoltage feedback). At time t4, this voltage adjustment is completed.

At time t5, the lighting control part 2911 switches off the main switch 2903e, to switch off the lighted LED. The lighting control part 2911 sets a voltage of the variable power source 2900 sufficiently high to prepare for the next lighting cycle. Setting the voltage of the variable power source 2900 to sufficiently high leads to improvement in responsiveness of lighting to a lighting command. In particular, due to the need for acquiring a large number of luminance images in the photometric stereo method, the time needed for one imaging is required to be reduced. In particular, when the workpiece 2 is moving, since the position of the workpiece 2 is displaced in each of the luminance images, the longer the imaging time, the more the accuracy in inspection image deteriorates. Therefore, the improvement in responsiveness of the illumination apparatus 3 reduces these problems.

<Lighting Pattern>

Figure 31:
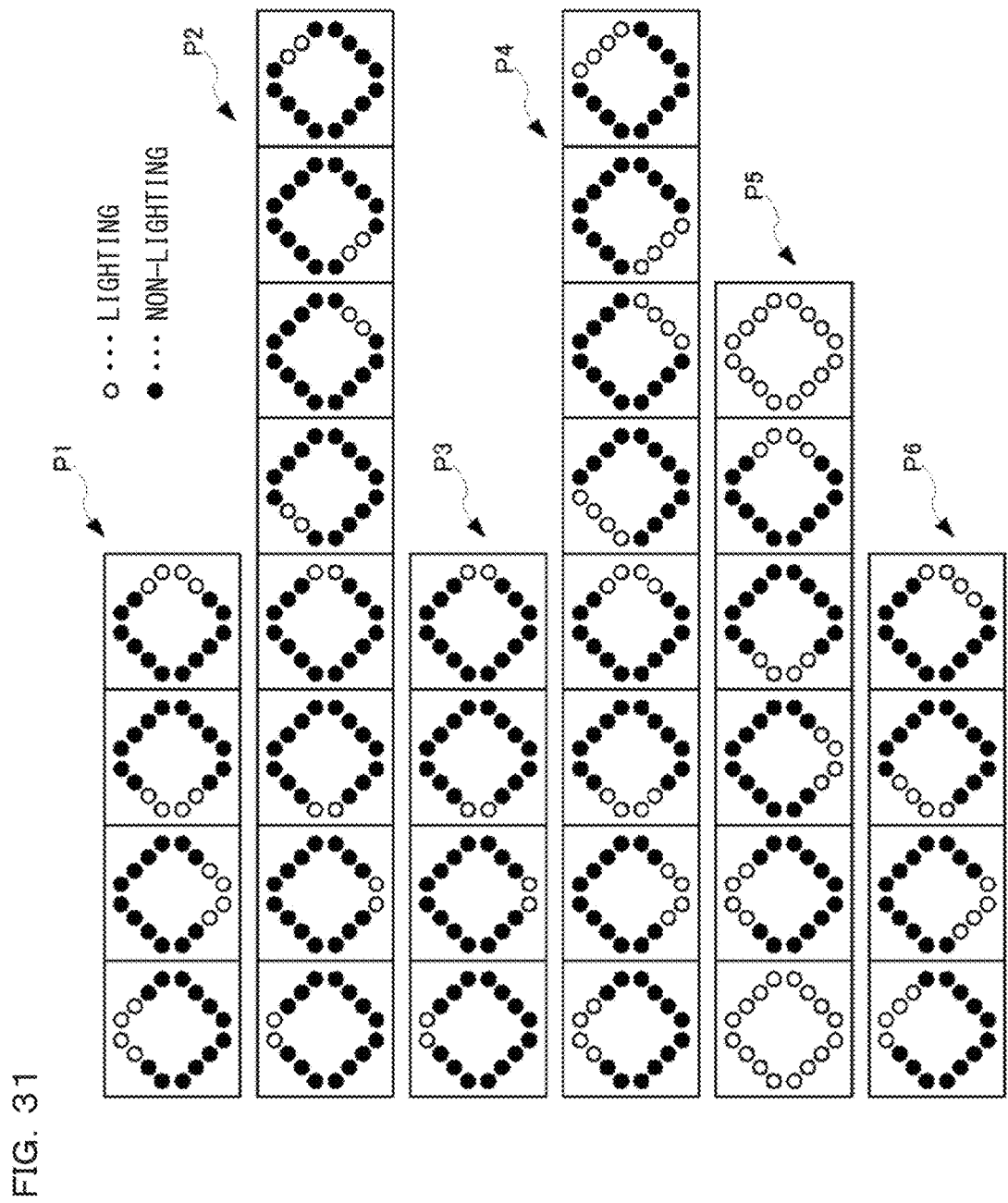
FIG. 31 is a view showing one example of lighting patterns.

FIG. 31 is a view showing one example of lighting patterns. A lighting pattern P1 is a pattern for realizing illumination from four illumination directions by using the 16 LEDs. A lighting pattern P2 is a pattern for realizing illumination from eight illumination directions by using the 16 LEDs. As compared to luminance images with four illumination directions, in luminance images with eight illumination directions, the accuracies in computing a normal vector n and a reflectance improve, and it is thus advantageous in improved accuracy in inspection image. Further, increasing the number of illumination directions improves the accuracy in detection of an edge existing in an oblique direction and the accuracy in detection of an outer shape of a circular workpiece. A lighting pattern P3 is a pattern for realizing illumination from four illumination directions by using the 16 LEDs. In the lighting pattern P3, the number of LEDs to be lighted in one lighting is one half as compared to the lighting pattern P1. Due to a decrease in area of the light sources, reflection of the light source onto the workpiece 2 can be reduced. A lighting pattern P4 is a pattern for realizing illumination from eight illumination directions by using the 16 LEDs. In the lighting pattern P4, the number of LEDs to be lighted in one lighting is twice as compared to the lighting pattern P2. This is advantageous in a case where a light amount is required as well as the accuracy in inspection image. A lighting pattern P5 is a pattern obtained by adding entire lighting before and after the lighting pattern P1 as a basic pattern. Two luminance images acquired by illumination from all directions are useful in estimating a movement amount of the workpiece 2. Accordingly, even in a case where imaging is executed while the workpiece 2 is being moved, it is possible to accurately create an inspection image in the luminance image while correcting the position of the workpiece 2. A lighting pattern P6 is a lighting pattern obtained by shifting the lighting start position just by one LED clockwise in the lighting pattern P1. In the present embodiment, since the illumination apparatus 3 can be moved independently of the camera 4, an installation direction of the camera 4 and an installation direction of the illumination apparatus 3 may be displaced from each other. Further, it is not easy to correct the position of the illumination apparatus 3 which is fixed once. Therefore, by correcting the lighting start position of the illumination apparatus 3 just by an amount corresponding to displacement between the installation direction of the camera 4 and the installation direction of the illumination apparatus 3, an illumination direction assumed in the luminance image can be matched with an actual illumination direction.

<Adjustment of Lighting Pattern Illumination Position>

Figure 32:
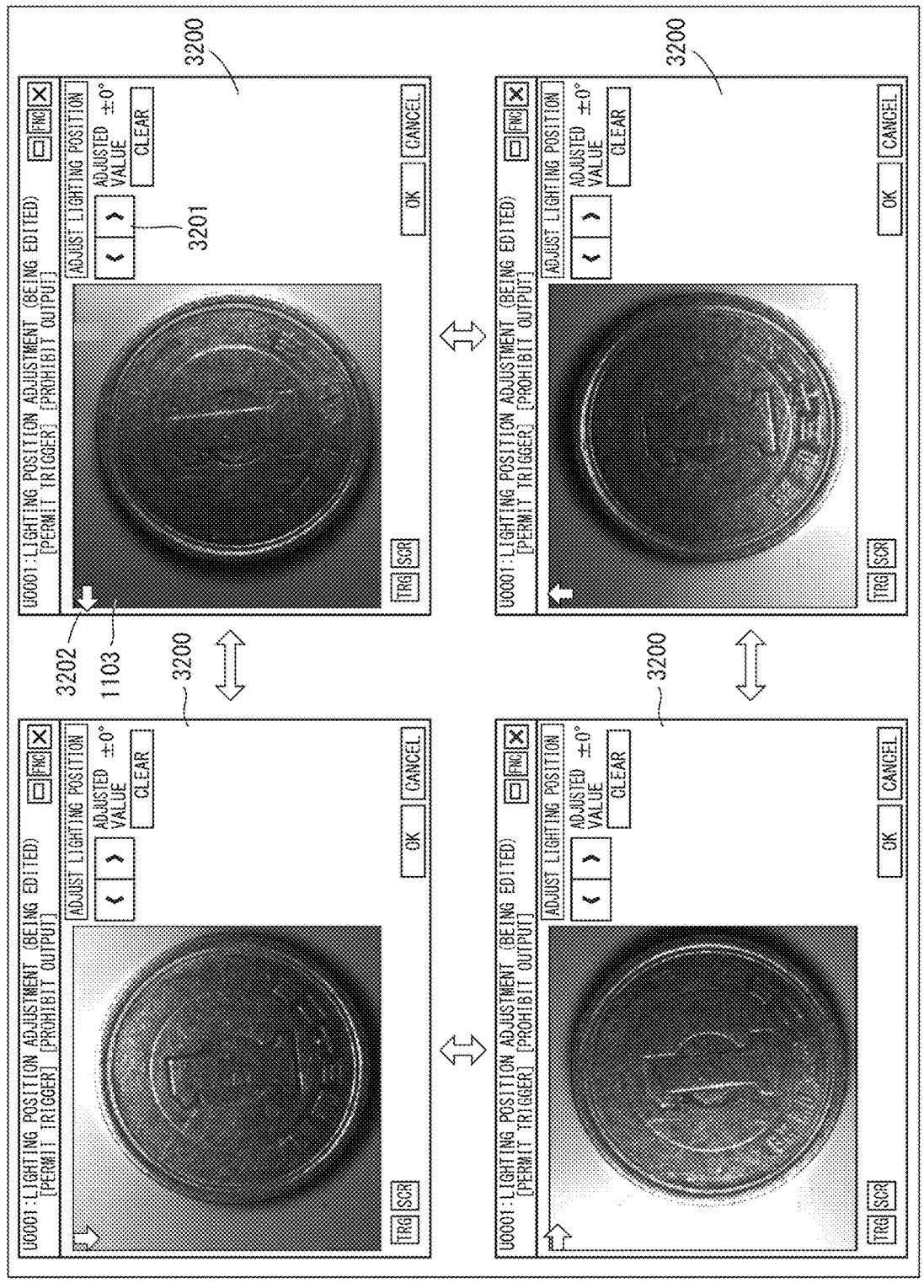
FIG. 32 is a view showing one example of the user interface.
Figure 33:
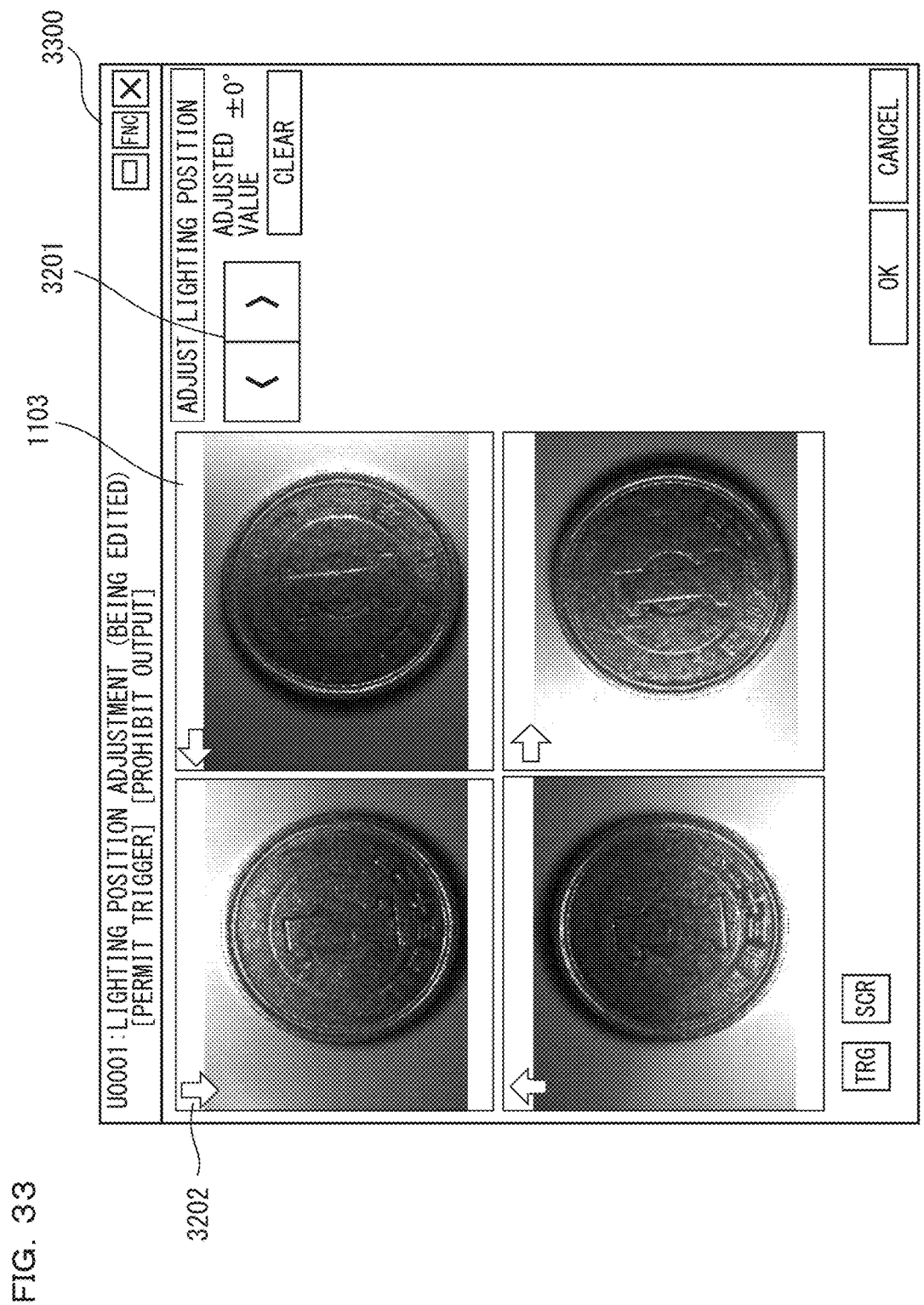
FIG. 33 is a view showing one example of the user interface.

FIG. 32 shows one example of a UI 3200 for adjusting the lighting start position. The inspection tool setting part 817 is provided with an adjustment part for adjusting the foregoing lighting start position, and sets the UI 3200 on the display part 7. The UI 3200 has the display region 1103 for displaying a luminance image, and an adjustment button 3201 for adjusting the lighting start position. The inspection tool setting part 817 superimposes and displays, on the luminance image, an arrow 3202 which is an icon for indicating an illumination direction assumed concerning the luminance image. This facilitates checking whether or not the illumination direction assumed concerning the luminance image matches with the actual illumination direction. The user operates the adjustment button 3201 through the input part 6. The inspection tool setting part 817 detects this adjustment operation, and notifies the illumination control part 812 of an adjustment amount. The illumination control part 812 transmits the adjustment amount of the lighting start position to the illumination controller 802. When receiving the adjustment amount through the communication part 2910, the lighting control part 2911 of the illumination controller 802 may save the adjustment amount into the storage part 803. Thereby, the lighting control part 2911 corrects the lighting start position in the lighting pattern designated by the lighting pattern data 2920 in accordance with the adjustment amount. In addition, in order to discriminate whether the adjustment is correct, the inspection tool setting part 817 may make the camera 4 execute imaging and acquire a luminance image through the imaging control part 813, to display the image in the display region 1103. In such a manner, the inspection tool setting part 817 may update and display the luminance image when the LED to be lighted is changed. In addition, as shown in FIG. 32, the display control part 851 may switch the luminance image to be displayed in the display region 1103 and display the luminance image on the display part 7. This will make illumination directions correctly settable in all luminance images with different illumination directions. FIG. 33 shows one example of a UI 3300 for adjusting the lighting start position. As shown in FIG. 33, the inspection tool setting part 817 may array and display four luminance images in the display region 1103. This allows the user to save labor of switching the four luminance images.

<Summary>

According to the present embodiment, the photometric processing part 811 calculates a normal vector of the surface of the workpiece 2 from a plurality of luminance images acquired by the camera 4 in accordance with the photometric stereo method, and performs accumulation computing of a pixel value of a pixel of interest by using a normal vector of a pixel adjacent to the pixel of interest with respect to an inclination image made up of pixel values based on the normal vector calculated from the plurality of luminance images and a reduced image of the inclination image, to generate an inspection image having the pixel value. In particular, according to the present embodiment, there is provided the characteristic size setting part 815 for setting a characteristic size which is a parameter for giving weight to a component of a reduced image that is used in the accumulation computing. As thus described, by introducing the concept of the characteristic size, a parameter can be easily set at the time of generating an inspection image from an image acquired by using the photometric stereo principle The characteristic size setting part 815 may set a plurality of characteristic sizes with respectively different values. In this case, the photometric processing part 811 may generate an inspection image with respect to each of the plurality of characteristic sizes set by the characteristic size setting part 815. It is considered that a suitable characteristic size differs according to a type of the inspection tool. Therefore, generating inspection images in accordance with a plurality of characteristic sizes with respectively different values is advantageous in selecting a more suitable image corresponding to the inspection.

The flaw inspection part 831 may execute flaw inspection on a plurality of inspection images generated by using respectively different characteristic sizes, and the determination part 840 may determine defectiveness/non-defectiveness of the workpiece 2 by using a result of the inspection by the flaw inspection part 831. Executing the flaw inspection on the plurality of inspection images eliminates the need for previously selecting one inspection image, which will be convenient for the user. The OCR part 832 may perform character recognition processing on a plurality of inspection images generated by using respectively different characteristic sizes, and the determination part 840 may determine defectiveness/non-defectiveness of the workpiece 2 by using a result of the character recognition by the OCR part 832. Performing the character recognition processing on the plurality of inspection images eliminates the need for previously selecting one inspection image, which will be convenient for the user.

Originally, a height image showing a height of the workpiece 2 can be generated by the photometric stereo method. However, measuring the height of the surface of the workpiece 2 requires a considerably strict setting for a positional relation between the camera 4 and the illumination apparatus 3. Meanwhile, out of images obtained by the photometric stereo method, shape information or texture (design) information can be used without using height information. For example, when a height image is to be used for the flaw inspection or the OCR, a strict setting for the camera 4 and the illumination apparatus 3 is not required. As thus described, when the inspection tool does not require accurate height data, it is possible to alleviate the arrangement conditions for the camera 4 and the illumination apparatus 3. Note that the number of illumination directions may be three or more.

The photometric processing part 811 may calculate a reflectance of the surface of the workpiece 2 along with a normal vector of the surface of the workpiece 2 from the plurality of luminance images acquired by the camera 4, to generate a reflectance image made up of pixel values based on the reflectance, and the determination part 840 may determine defectiveness/non-defectiveness of the workpiece 2 by using the reflectance image. This is because there also exists an inspection tool in which a reflectance image is suitably used for the inspection. The photometric processing part 811 may generate an inclination image made up of pixel values based on a normal vector of the surface of the workpiece 2 from the plurality of luminance images acquired by the camera 4, and the determination part 840 may determine defectiveness/non-defectiveness of the workpiece 2 by using the inclination image. This is because there also exists an inspection tool in which an inclination image is suitably used for the inspection. The determination part 840 may determine defectiveness/non-defectiveness of the workpiece 2 by using a luminance image. This is because there also exists an inspection tool in which a luminance image before being processed into an inclination image or a reflectance image is suitably used for the inspection. The determination part 840 may determine defectiveness/non-defectiveness of the workpiece 2 by using at least one luminance image out of a plurality of luminance images with respectively different illumination directions. Since there exists a flaw or the like that becomes clear by differences in the illumination direction, a luminance image obtained by illuminating the workpiece 2 from a certain direction is suitable for detecting such a flaw.

The determination part 840 may simultaneously light all the light sources of the illumination apparatus 3 and determine defectiveness/non-defectiveness of the workpiece 2 by using a luminance image acquired by the camera 4. That is, by using a so-called all-directional illumination image, whether the workpiece 2 is defective or non-defective may be determined. For example, the all-directional illumination image may be suitable for calculation of an area of a certain portion of the workpiece 2 or measurement of a length of a terminal.

The determination part 840 may synthesize a plurality of luminance images with respectively different illumination directions and determine defectiveness/non-defectiveness of the workpiece 2 by using the generated synthesized luminance image. The synthesized luminance image is an image similar to the all-directional illumination image. Therefore, by use of the synthesized luminance image in place of the all-directional illumination image, it is possible to execute the inspection without acquiring the all-directional illumination image. In the case where an all-directional illumination image is required, it is necessary to acquire four luminance images with respectively different illumination directions and one all-directional illumination image obtained by simultaneous illumination from four directions. That is, five times of illumination and five times of imaging are required. On the other hand, when the synthesized luminance image is used, four times of illumination and four times of imaging may be performed. In such a manner, adopting the synthesized luminance image can reduce a processing load of the processor 810 when a plurality of inspection images are required to be processed in a short period of time. Further, as the number of acquired images is increased, it becomes necessary to lower a conveying speed of the line 1. However, in the present embodiment, since the number of acquired images can be reduced, the conveying speed of the line 1 can be increased.

The storage device 820 may store and hold an inspection image. The determination part 840 or the image processing part 830 may read the inspection image from the storage device 820 and execute the inspection, to determine defectiveness/non-defectiveness of the workpiece 2 based on the inspection result. Note that the storage device 820 may be any of the internal memory, the portable type storage medium, and the network storage. For example, when an inspection image is stored into the portable type storage medium or the network storage, it is possible to perform inspection processing in an apparatus different from the apparatus that has generated the inspection image.

The storage device 820 may store a plurality of inspection images generated by applying characteristic sizes with respectively different values. In addition to the inspection image, the storage device 820 may store at least one of an inclination image and a reflectance image. The image selection part 816 may select one inspection image out of a plurality of inspection images. Further, the inspection tool setting part 817 may set an inspection tool for the inspection image selected by the image selection part 816. Among the plurality of inspection images generated by applying the characteristic sizes with respectively different values, an inspection image not required for the inspection may exist. Hence, the user may set an inspection image in accordance with an inspection tool.

As described using FIG. 15 and the like, the image processing part 830 may execute a pattern search by using a reference image acquired from a non-defective product, to set an inspection region. The determination part 840 may determine defectiveness/non-defectiveness of the workpiece 2 by using a result of the inspection executed in the inspection region. The inspection region is, for example, a character recognition region.

As described using FIG. 11 and FIGS. 21 to 26, the image selection part 816 may select an image, which is to be saved or outputted, out of a plurality of luminance images acquired by the camera 4 and an inspection image. Further, the image selection part 816 may select an image, which is to be saved or outputted, out of a plurality of luminance images, an inspection image, a luminance image acquired by lighting all of a plurality of light sources provided in the illumination apparatus 3, and a synthesized luminance image obtained by synthesizing the plurality of luminance images. Moreover, the image selection part 816 may select an image, which is to be saved or outputted, out of a plurality of inspection images with respectively different characteristic sizes. Furthermore, the image selection part 816 may select an image, which is to be saved or outputted, out of a plurality of luminance images, an inspection image, and a reflectance image whose pixel value is a reflectance of the surface of the workpiece 2. As thus described, allowing an image related to the inspection to be selected as appropriate will facilitate saving or outputting of a desired image.

The condition setting part 819 for setting a condition for saving or outputting an image may further be provided. For example, as described using FIGS. 22 and 26, the condition setting part 819 may, for example, set one of the mode for constantly saving or outputting an image, and the mode for saving or outputting an image when the determination part 840 determines that the workpiece 2 is not a non-defective product. As described using FIGS. 21 to 26, the processor 810 may judge whether or not the condition for saving or outputting an image is satisfied before or after the determination part 840 completes the determination. For example, whether or not an image is saved may be judged at the time point when the inspection is completed in the inspection flow, or whether or not an image is saved may be judged in any step of the inspection flow. In particular, in the latter case, it is also possible to save an intermediate image generated in the middle of the inspection flow. Such an intermediate image will be useful at the time of searching for a cause of failure in the inspection and adjusting a control parameter.

According to the present embodiment, the illumination apparatus 3 has a plurality of LEDs 2803 arranged in a substantially annular form, the light diffusion member 2703 for diffusing light to be emitted from each of the plurality of LEDs 2803, and the lighting control part 2911 for lighting the plurality of light sources in accordance with a predetermined lighting pattern when designated to start lighting. In particular, the illumination apparatus 3 moves independently of the camera 4, to adjust a distance to the workpiece 2. Therefore, in accordance with the type or the placement of a workpiece, it is possible to bring the illumination apparatus 3 away from a workpiece to use regular reflective light, or brings the illumination apparatus 3 close to the workpiece to use diffused reflective light. The illumination controller 802 such as the lighting control part 2911 may be arranged outside the illumination apparatus 3.

As described using FIGS. 28C to 28E, the shading member 2805 may be arranged between two adjacent LEDs 2803 out of the plurality of LEDs 2803. Thereby, the balance of uniformity of light amounts and independency of light sources are kept as to the two adjacent LEDs 2803.

The illumination apparatus 3 may have the LED substrate 2802 as the first substrate on which the plurality of LEDs 2803 are mounted, and the control substrate 2801 as the second substrate on which the lighting control part 2911 is mounted. Separating the substrates can reduce an influence of heat generation of the plurality of LEDs 2803.

The description has been given of the example of arranging the plurality of LEDs 2803 in the annular form by using FIGS. 27 and 28. The annular arrangement is advantageous in realizing parallel light from each illumination direction. Note that the annular arrangement is merely one example, and regular polygonal arrangement or the like may be made.

For example, 16 LEDs 2803 may be arranged at respective vertexs of a regular hexadecagon.

The illumination apparatus 3 may have the storage part 803 in which a lighting pattern of the plurality of LEDs 2803 is stored. When designated to start lighting by a control signal or a trigger signal, the lighting control part 2911 may light the plurality of LEDs 2803 in accordance with the lighting pattern stored in the storage part 803. As thus described, the lighting control part 2911 may light the plurality of LEDs 2803 in accordance with the lighting pattern data 2920 stored in the storage part 803 and specified by a control signal received via the signal line 8. Hence, the number of signal lines can be significantly reduced compared to the case of arranging the signal line 8 for each LED. For example, when 16 LEDs 2803 are to be controlled from the image processing apparatus 5, at least 17 signal lines are required. However, since the signal line 8 which can transmit a control signal for designating a lighting pattern can be adopted in the present embodiment, it is possible to reduce the number of signal lines, so as to reduce a cost of cable that connects the image processing apparatus 5 and the illumination apparatus 3.

The storage part 803 may store a plurality of lighting patterns (P1, P3, or the like) in which the number of simultaneously lighted light sources are different. Hence, it is possible to easily change a light amount to one half or twice as large. The storage part 803 may store a plurality of lighting patterns (P1, P2, or the like) with respectively different illumination directions. Thereby, luminance images with different illumination directions can be easily obtained. The storage part 803 may store a plurality of lighting patterns (P1, P3, P5, P6) for illuminating the inspection target in order from four directions, or may store lighting patterns (P2, P4) for illuminating the inspection target in order from eight directions. Hence, it is possible to easily change a light amount to one half or twice as large. The storage part 803 may store a lighting pattern (P5 or the like) for simultaneously lighting all of a plurality of light sources. Thereby, an all-directional illumination image can be easily obtained. An estimation part 833 of the image processing part 830 estimates a position of the workpiece 2 from the all-directional illumination image. As the lighting pattern P5 shows, the illumination control part 812 and the imaging control part 813 make all of the plurality of LEDs 2803 simultaneously lighted at the first timing, and make the camera 4 acquire a first luminance image. Further, as the lighting pattern P5 shows, the illumination control part 812 and the imaging control part 813 make all of the plurality of LEDs 2803 simultaneously lighted at N-th timing (the sixth timing in the lighting pattern P5), and make the camera 4 acquire a second luminance image. The estimation part 833 estimates a movement amount of the workpiece 2 from the first luminance image and the second luminance image. That is, in the lighting pattern P5, the estimation part 833 estimates the position of the workpiece 2 in the luminance images at the second timing and the fifth timing from the luminance image at the first timing and the luminance image at the sixth timing. The photometric processing part 811 acquires a movement amount of the workpiece 2 at each timing from the estimation part 833, and corrects each luminance image such that the positions of the workpiece 2 in the luminance images at the second timing and the fifth timing match with each other. The photometric processing part 811 then creates an inspection image from the corrected luminance images. In order to estimate the position of the workpiece 2, it is advantageous to use an all-directional illumination image, thereby requiring a lighting pattern that includes simultaneous lighting of all of the plurality of LEDs 2803 like the lighting pattern P5.

As described using FIG. 29, each predetermined number (for example, 4) of LEDs 2803 out of the plurality of LEDs 2803 forms a light source group, and a plurality of LEDs 2803 may be connected in series in each light source group. Each of the switches 2903a to 2903d, which can be switched on/off by the lighting control part 2911, is connected in parallel to each of the plurality of LEDs 2803a to 2803d. Hence it is possible to freely switch lighting and non-lighting of the plurality of LEDs 2803a to 2803d in accordance with the lighting pattern. That is, a variety of lighting patterns can be adopted.

As described using FIG. 29, the lighting control part 2911 may control the variable power source 2900 for supplying a voltage to each of the plurality of LEDs 2803, the variable constant current source 2901 for adjusting a current flowing through the plurality of LEDs 2803, and the main switch 2903e for switching on/off of the variable constant current source 2901. That is, as described using FIG. 30, a voltage supplied by the variable power source is sufficiently high, and then the lighting control part 2911 may switch the switch that is connected in parallel to each of the plurality of LEDs 2803 in accordance with the lighting pattern, and switch on the main switch 2903e, to light any of the plurality of LEDs 2803 in accordance with the lighting pattern. Thereby, it is possible to achieve high responsiveness of lighting and improvement in power efficiency. The lighting control part 2911 may control a voltage of the variable power source 2900 in accordance with a voltage value that is fed back from the variable constant current source 2901 such that an overvoltage is not applied to the variable constant current source 2901. Thereby, it is possible to protect the variable constant current source 2901 from an overvoltage.

What is claimed is:

1. An inspection apparatus comprising:
    an illumination section which has a plurality of light segments to illuminate the inspection target from three or more illumination directions;
    a processor for controlling the illumination section to light the plurality of light segments;
    an imaging section for capturing a plurality of luminance images of an inspection target;
    an inspection image generating section for obtaining a normal vector of a surface of the inspection target based on the three or more luminance images acquired by the imaging section and generating a shape image based on the normal vector by a photometric stereo method;
    an image selection section for selecting an inspection image out of the plurality of luminance images captured by the imaging section and the shape image generated by the inspection image generating section; and
    an inspection tool setting section for setting an inspection tool on the selected image by the image selection section.

2. The inspection apparatus according to claim 1, wherein the inspection image generating section generates an inclination image made up of pixel values based on the normal vector.

3. The inspection apparatus according to claim 2, wherein the image selection section accepts the image selection out of the plurality of luminance images, the shape image, and the inclination image.

4. The inspection apparatus according to claim 1, wherein the inspection image generating section generates all-directional illumination image which is a luminance image acquired by lighting all of the light segments.

5. The inspection apparatus according to claim 4, wherein the image selection section accepts the image selection out of the plurality of luminance images, the shape image, and the all-directional illumination image.

6. The inspection apparatus according to claim 1, wherein the inspection image generating section generates a texture image based on a reflectance of surface of the inspection target and the image selection section accepts the image selection out of the plurality of luminance images, the shape image and the texture image.

\* \* \* \* \*